United States Patent [19]
Scholz et al.

[11] Patent Number: 6,019,997
[45] Date of Patent: *Feb. 1, 2000

[54] HYDROALCOHOLIC COMPOSITIONS FOR TRANSDERMAL PENETRATION OF PHARMACEUTICAL AGENTS

[75] Inventors: Matthew T. Scholz, Woodbury; Robert A. Asmus, Hudson; John C. Hedenstrom, St. Paul, all of Minn.

[73] Assignee: Minnesota Mining and Manufacturing, St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/781,097

[22] Filed: Jan. 9, 1997

[51] Int. Cl.$^7$ ............................................. A61F 13/00
[52] U.S. Cl. .................. 424/449; 514/937; 514/946; 514/947
[58] Field of Search ............... 424/449; 514/937, 514/946, 947

[56] References Cited

U.S. PATENT DOCUMENTS

| | | | |
|---|---|---|---|
| 2,054,989 | 9/1936 | Moore | 167/58 |
| 2,153,143 | 4/1939 | Figg, Jr. et al. | 87/5 |
| 2,678,902 | 5/1954 | Mehaffey | 167/91 |
| 3,131,152 | 4/1964 | Klausner | 252/305 |
| 3,131,153 | 4/1964 | Klausner | 252/305 |
| 3,395,214 | 7/1968 | Mummert | 424/47 |
| 3,415,939 | 12/1968 | Minton | 424/357 |
| 3,840,465 | 10/1974 | Knowles et al. | 252/90 |
| 4,006,218 | 2/1977 | Sipos | 424/54 |
| 4,199,564 | 4/1980 | Silver et al. | 421/80 |
| 4,202,881 | 5/1980 | Gross et al. | 424/70 |
| 4,254,104 | 3/1981 | Suzuki | 424/170 |
| 4,464,293 | 8/1984 | Dobrin | 252/547 |
| 4,478,853 | 10/1984 | Chaussee | 424/358 |
| 4,501,834 | 2/1985 | Su | 524/28 |
| 4,511,486 | 4/1985 | Shah | 252/90 |
| 4,542,012 | 9/1985 | Dell | 424/28 |
| 4,559,226 | 12/1985 | Fogel et al. | |

(List continued on next page.)

FOREIGN PATENT DOCUMENTS

| | | |
|---|---|---|
| B-72440/87 | 11/1987 | Australia . |
| 0 014 502 A1 | 8/1980 | European Pat. Off. . |
| 0 223 681 A1 | 5/1987 | European Pat. Off. . |

(List continued on next page.)

OTHER PUBLICATIONS

Richard H. Guy et al., "Selection of Drug Candidates for Transdermal Drug Delivery", *Transdermal Drug Delivery: Developmental Issues and Research Initiatives*, eds: Jonathan Hadgraft and Richard H. Guy, Marcell Dekker, Inc., New York, NY (1989).

"Percutaneous Penetration Enhancers", Eds: Eric W. Smith and Howard I. Maibach, CRC Press, Inc., Boca Raton, FL (1995).

(List continued on next page.)

*Primary Examiner*—D. Gabrielle Brouillette
*Attorney, Agent, or Firm*—Robert W. Sprague; Jeffrey J. Hohenshell

[57] ABSTRACT

Hydroalcoholic compositions useful for the enhancement of the transdermal delivery of a pharmaceutical agent, methods of preparation, transdermal delivery systems, and methods of delivering the pharmaceutical agent are provided. The composition includes a lower alcohol and water in a weight ratio of at least about 20:80, a pharmaceutical agent, and an emulsifier system.

56 Claims, 1 Drawing Sheet

U.S. PATENT DOCUMENTS

| | | | |
|---|---|---|---|
| 4,584,192 | 4/1986 | Dell et al. | 424/81 |
| 4,671,957 | 6/1987 | Holtshousen | 424/80 |
| 4,695,453 | 9/1987 | Tuominen et al. | 424/81 |
| 4,719,239 | 1/1988 | Muller et al. | 514/23 |
| 4,752,612 | 6/1988 | Saito et al. | 514/420 |
| 4,806,262 | 2/1989 | Snyder | 252/90 |
| 4,831,023 | 5/1989 | Garlen et al. | |
| 4,839,167 | 6/1989 | Yamamoto et al. | 424/71 |
| 4,883,660 | 11/1989 | Blackman et al. | |
| 4,915,934 | 4/1990 | Tomlinson | 424/45 |
| 4,931,282 | 6/1990 | Asmus et al. | 424/448 |
| 4,956,170 | 9/1990 | Lee | 424/81 |
| 4,957,908 | 9/1990 | Nelson | 514/55 |
| 4,981,678 | 1/1991 | Tomlinson | 424/45 |
| 5,120,716 | 6/1992 | Miyazawa et al. | 514/23 |
| 5,128,123 | 7/1992 | Brewster et al. | 424/65 |
| 5,149,719 | 9/1992 | Ferber et al. | 514/772 |
| 5,164,107 | 11/1992 | Khan et al. | 252/106 |
| 5,167,950 | 12/1992 | Lins | 424/47 |
| 5,180,061 | 1/1993 | Khan et al. | 206/570 |
| 5,180,584 | 1/1993 | Sebag et al. | 424/401 |
| 5,223,261 | 6/1993 | Nelson et al. | 424/443 |
| 5,225,473 | 7/1993 | Duan | 524/388 |
| 5,232,691 | 8/1993 | Lemole | 424/78.02 |
| 5,298,242 | 3/1994 | Vanlerberghe et al. | 424/78.36 |
| 5,334,388 | 8/1994 | Hoang et al. | 424/402 |
| 5,362,484 | 11/1994 | Wood et al. | 424/70 |
| 5,409,966 | 4/1995 | Duan et al. | 522/152 |
| 5,484,597 | 1/1996 | Slavtcheff et al. | 424/401 |
| 5,512,199 | 4/1996 | Khan et al. | 252/106 |
| 5,585,092 | 12/1996 | Trandai et al. | 424/65 |
| 5,626,853 | 5/1997 | Bara et al. | 424/401 |

FOREIGN PATENT DOCUMENTS

| | | |
|---|---|---|
| 0 260 641 A2 | 3/1988 | European Pat. Off. |
| 0 289 160 A1 | 4/1988 | European Pat. Off. |
| 0 381 618 A1 | 8/1990 | European Pat. Off. |
| 0 451 949 A1 | 10/1991 | European Pat. Off. |
| 0 522 624 A1 | 1/1993 | European Pat. Off. |
| 0 689 767 A2 | 1/1996 | European Pat. Off. |
| 0 745 389 A1 | 12/1996 | European Pat. Off. |
| 788 811 | 10/1935 | France . |
| 2 406 438 | 5/1979 | France . |
| 34 16 777 A1 | 11/1985 | Germany . |
| 3632030 A1 | 3/1988 | Germany . |
| 80 92 078 | 4/1996 | Japan . |
| 1 527 781 | 10/1978 | United Kingdom . |
| 93/07903 | 4/1993 | WIPO . |
| WO 94/13354 | 6/1994 | WIPO . |
| 95/03772 | 2/1995 | WIPO . |
| WO 97/00667 | 1/1997 | WIPO . |

OTHER PUBLICATIONS

BIOISIS Abstract 80:188 400, Abstract of *Zentralbl Bakteriol Parasitenkd Infektionskr Hyg Erst Abt Orig Reihe B Hyg Krankaenhaushyg Betriebshyg Praev Med,* 168, pp. 5–6 (1979).

BIOSIS Abstract 86:434 601, Abstract of *Hyg. Med.,* 11, pp. 238–241 (1986).

Bulletin No. 51–0001–259, Speciality Chemicals of ICI America of Wilmington, DE, 1990.

J.L. Cohen et al., "Penetration of 5–Fluorouracil In Excised Skin", *The J. of Investigative Dermatology,* 62, pp. 507–509 (1974).

CTFA Cosmetic Ingredient Handbook, Published by The Cosmetic, Toiletry and Fragrance Association, Inc., pp. 37, 64–65, 78, 81 (1988).

G.M. Eccleston, "Application of Emulsion Stability Theories to Mobile and Semisolid O/W Emulsions", *Cosmetics & Toiletries,* 101, pp. 73–92 (1986).

G.M. Eccleston, "Influence of long chain alcohols (or acids) and surfactants on the stabilities and consistencies of cosmetic lotions and creams", *Cosmetics and Toiletries,* 92, pp. 21–28 (1977).

E.D. Goodard et al., "Novel gelling structures based on polymer/surfactant systems", *J. Soc. Cosmet. Chem.,* 42, pp. 19–34 (1991).

P.B. Price, "Reevaluation Of Ethyl Alcohol As A Germicide", *Archives of Surgery,* pp. 492–502 (1950).

R.B. Stoughton, "Vasoconstrictor Activity and Percutaneous Absorption of Glucocorticosteroids", *Arch. Derm.,* 99, pp. 753–756 (1969).

"Textbook of Polymer Science", F.W. Billmeyer, Ed.; Wiley–Interscience, NY; $2^{nd}$ Edition; pp. 84–85 (1971).

HYDROALCOHOLIC COMPOSITIONS FOR TRANSDERMAL PENETRATION OF PHARMACEUTICAL AGENTS

FIELD OF THE INVENTION

The present invention relates to compositions useful as vehicles for transdermal penetration of pharmaceutical agents. More specifically, the invention relates to hydroalcoholic compositions that serve to enhance the transdermal delivery of pharmaceutical agents through the skin of humans and other mammals.

BACKGROUND OF THE INVENTION

A principal function of the skin is to retain essential fluids while protecting against harmful intruding agents. Therefore, the skin can be a formidable barrier for delivery of many pharmaceutical agents (e.g., medicaments, drugs, prodrugs, etc.). Many compositions have been described in the literature to enhance the transdermal penetration of certain pharmaceutical agents. Such compositions typically include chemical penetration enhancers such as alkanes, alkenes, alcohols, amides, amines, amine oxides, carboxylic acids, ethers, esters, halocarbons, ketones, and sulfoxides.

Chemical penetration compositions have also been described that, for one purpose or another, involve the use of either lower or higher alcohols, or occasionally both lower and higher alcohols. See, e.g., U.S. Pat. No. 4,752,612 (Saito et al.), and U.S. Pat. No. 5,149,719 (Ferber et al.), and International Publication No. WO 93/07903 (Deckner). Penetration enhancing compositions involving the use of both lower and higher alcohols in an aqueous system (i.e., hydroalcoholic systems) are described (see, e.g., U.S. Pat. No. 4,006,218 (Sipos)); however, such systems can be quite irritating and often include additional penentration enhancers that increase this irritation. Thus, there is still a need for hydroalcoholic compositions containing a pharmaceutical agent that delivers the pharmaceutical agent transdermally.

SUMMARY OF THE INVENTION

The present invention provides hydroalcoholic compositions containing pharmaceutical agents useful for transdermal delivery, transdermal delivery systems containing such compositions, methods of preparing the hydroalcoholic compositions, and methods of delivering the pharmaceutical agent transdermally to a patient.

One embodiment of the invention is a hydroalcoholic composition useful for the enhancement of the transdermal delivery of a pharmaceutical agent, the composition comprising: (a) a lower alcohol and water in a weight ratio of at least about 20:80; (b) a pharmaceutical agent; and (c) an emulsifier system comprising at least two emulsifiers, each emulsifier being present in an amount of at least about 0.05% by weight, based on the total weight of the composition; wherein each emulsifier: (i) is of the formula $(R)_a(L)_b$ wherein "R" represents a hydrophobic group, "L" represents a hydrophilic group, and "a" and "b" are independently 1–4; and (ii) is selected such that the composition free of auxiliary thickeners has a viscosity of at least about 4,000 centipoise at 23° C. Preferably, the composition is a stable hydroalcoholic composition.

Such compositions are preparable by combining these components, specifically using various methods described herein. One such method involves: preparing an emulsifier system comprising at least two emulsifiers, each emulsifier being present in an amount of at least about 0.05% by weight, based on the total weight of the composition; wherein each emulsifier is of the formula $(R)_a(L)_b$ wherein "R" represents a hydrophobic group, "L" represents a hydrophilic group, and "a" and "b" are independently 1–4 and is selected such that the resultant hydroalcoholic composition free of auxiliary thickeners has a viscosity of at least about 4,000 centipoise at 23° C.; and combining a hydroalcoholic solvent system with the emulsifier system and a pharmaceutical agent to form a hydroalcoholic composition.

A second method involves: heating an emulsifier system comprising at least two emulsifiers, each emulsifier being present in an amount of at least about 0.05% by weight, based on the total weight of the composition; wherein each emulsifier is of the formula $(R)_a(L)_b$ wherein "R" represents a hydrophobic group, "L" represents a hydrophilic group, and "a" and "b" are independently 1–4 and is selected such that the resultant hydroalcoholic composition free of auxiliary thickeners has a viscosity of at least about 4,000 centipoise at 23° C.; combining the heated emulsifier system with water; adding a lower chain alcohol to the water/emulsifier system; and adding a pharmaceutical agent to form a hyddroalcoholic composition.

Another embodiment of the invention is a hydroalcoholic composition useful for the enhancement of the transdermal delivery of a pharmaceutical agent, the composition comprising: (a) a lower alcohol and water in a weight ratio of at least about 20:80; (b) a pharmaceutical agent; and (c) an emulsifier system comprising at least one emulsifier present in an amount of at least about 0.05% by weight, based on the total weight of the composition; wherein the emulsifier is a compound of the formula

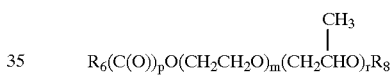

wherein $R_6$ is a straight or branched alkyl or alkenyl hydrocarbon chain of at least 12 carbon atoms, m=0–200, p=0 or 1, and r=0–50, and $R_8$=H or —C(O)—$R_{12}$, wherein $R_{12}$ is an alkyl group of 1–36 carbon atoms optionally substituted by N,O or S atoms, or an aralkyl group of 6 to 36 carbon atoms. Such compositions are preparable by combining these components, specifically using various methods described herein. Methods for preparing compositions that include this class of emulsifier are similar to the embodiments described above.

The present invention also provides transdermal delivery systems. Such systems include the hydroalcoholic compositions described above and means for delivery of the composition to the skin of a patient. Such means for delivery can be the composition itself (i.e., as a lotion), or it can be some other commonly used delivery device, such as a reservoir device. Methods for delivering the pharmaceutical agents contained in the compositions of the present invention transdermally to a patient are also provided.

Definitions

"Ambient temperature" as used herein refers to the temperature range of about 21–25° C.

"Auxiliary thickeners" as used herein refers to additives (other than the emulsifiers which can greatly increase the viscosity of the system as described below) which increase the viscosity of the solvent phase even in the absence of the emulsifier system described herein. Certain auxiliary thickeners may act synergistically with the emulsifier system to increase the viscosity of the resultant formula. Auxiliary thickeners include, but are not limited to, soluble and swellable polymers (typically, of a number average molecular weight significantly higher than about 4000, often higher than about 20,000 and more often higher than about 100,000) and associative colloidal thickeners such as silica, magnesium aluminum silicate, and the like.

"Emollient" as used herein refers broadly to materials which are capable of maintaining or improving the moisture level, compliance, or appearance of the skin when used repeatedly.

"Emulsifier" as used herein is synonymous with "surfactant" and refers to molecules comprising hydrophilic (polar) and hydrophobic (non-polar) regions on the same molecule. Such molecules have a number average molecular weight of less than about 4000, and usually less than about 2500.

"Emulsifier System" as used herein refers to at least one, and preferably a combination of at least two, emulsifiers.

"Emulsion" as used herein refers to a stable dispersion of one liquid in a second immiscible liquid. Emulsion also refers to stable dispersions of a solid in an immiscible liquid wherein the solid was formed by cooling below the freezing point of the solid composition.

"Lotion" means liquid or cream, free of any propellant.

"Melt temperature" ($T_m$) as used herein refers to the temperature at which compositions or emulsions of the present invention dramatically lose viscosity.

"Penetration Enhancer" as used herein is a compound other than a lower alcohol or emulsifier system component which when added to the composition results in an increased flux of pharmaceutical agent present in the composition as determined by the Cumulative Flux Text Method described herein.

"Pharmaceutical Agent" as used herein refers to a compound that is intended to be delivered transdermally (i.e., through the skin into the circulatory system) to a mammal to alter biological function to treat, cure, and/or prevent disease or abnormal conditions. It includes medicaments, drugs, prodrugs, etc., but does not include topical agents that are primarily used for treatment of skin conditions.

"Solvent," "solvent system," or "hydroalcoholic solvent" as used herein refer to the alcohol and water combination in the present invention.

"Stable" as used herein refers to a composition that displays less than or equal to 10% by volume separation after centrifuging at 1545×g for 30 minutes at ambient temperature.

"Surfactant" as used herein is synonymous with "emulsifier," the definition of which is given above.

DETAILED DESCRIPTION OF THE INVENTION

Figure 1:
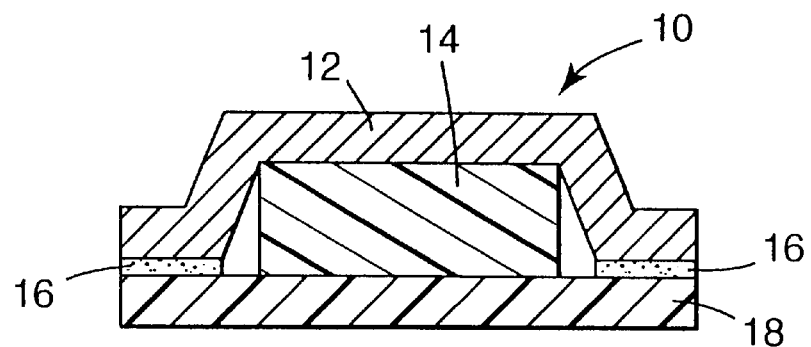
FIG. 1 is a cross-sectional view of a transdermal delivery system in the form of a reservoir device.

The present invention provides stable hydroalcoholic compositions useful as products for delivery of pharmaceutical agents (e.g., medicaments) transdermally (i.e., through the skin). The compositions of the present invention include a lower chain alcohol, water, an emulsifier system, and a pharmaceutical agent.

Such compositions provide enhanced transdermal delivery of a pharmaceutical agent relative to the same pharmaceutical agent in water alone (whether in the form of a solution, suspension, or dispersion). Transdermal delivery can be measured as the cumulative flux of the pharmaceutical agent. Cumulative flux can be measured according to the test procedure described below. Preferred compositions of the present invention have a cumulative flux of at least about three times (more preferably at least about ten times, and most preferably at least about fifty times) that of the same pharmaceutical agent in water.

Preferably, the compositions of the present invention form low irritation transdermal delivery vehicles for pharmaceutical agents. An additional benefit of certain preferred compositions of the present invention is the inherent antimicrobial activity provided by the lower chain alcohol. This can result in extended-wear transdermal patches without the concern of microbial proliferation under the patch. This may be especially beneficial when delivering steroids or other medications that can reduce the immune system potential on immunocompromised patients.

Hydroalcoholic Solvent System

The compositions of the present invention include one or more alcohols in combination with water, thereby producing a hydroalcoholic solvent system. The alcohol used in the compositions of the present invention is a lower chain hydrocarbon alcohol (referred to herein as a "lower alcohol"), particularly a C1–C4 alcohol (i.e., an alcohol having 1–4 carbon atoms). In preferred embodiments, the alcohol is ethanol, 2-propanol (i.e., isopropanol), or n-propanol. In more preferred embodiments, the alcohol is ethanol or isopropanol. Isopropanol and ethanol are preferred alcohols because they provide exceptional penetration enhancement for a wide variety of pharmaceutical agents. Furthermore, they have an acceptable odor to health practitioners and patients.

The lower alcohol to water ratio in the compositions of the present invention is at least about 20:80 by weight (i.e., the lower alcohol is present in an amount of at least about 20 weight percent, and the water is present in an amount of about 80 weight percent, based only on the weight of the water plus the lower alcohol within the composition). Typically, compositions of the present invention have an alcohol to water ratio of no greater than about 99:1 by weight. Compositions having an alcohol to water ratio within a range of about 30:70 to 80:20 by weight (i.e., 30–80 weight percent alcohol and 20–70 weight percent water, based only on the weight of water plus lower alcohol in the composition) provide particularly efficacious transdermal delivery. In particularly preferred embodiments, the lower alcohol to water ratio is within a range of about 40:60 to 70:30. Higher ratios of lower alcohol to water are used in preferred embodiments where enhanced flux and/or antimicrobial activity is desired. To enhance antimicrobial activity, the lower alcohol to water ratio is generally at least about 50:50 and typically no greater than about 90:10.

Emulsifier System

The emulsifier system useful in the compositions of the present invention affects the rheology and cosmetic attributes of the final composition. In certain conventional hydroalcoholic systems, such as those described in U.S. Pat. No. 4,956,170 (Lee) and U.S. Pat. No. 5,167,950 (Lins), International Publication No. WO 93/07903 (Deckner et al.), highly charged ionic systems such as polyacrylic acids and quaternary acrylates are used as thickeners to effect rheology. These highly charged polymeric thickeners are incompatible with many pharmaceutical agents of opposite charge, however. In other hydroalcoholic systems, such as those described in U.S. patent application Ser. Nos. 08/493,714 and 08/493,695 (both of which were filed on Jun. 22, 1995 and assigned to 3M Company), nonionic, anionic, cationic, or zwitterionic emulsifiers are used as thickeners, without the need for a polymeric thickener such as polyacrylic acid. Prior to the present invention, hydroalcoholic compositions containing such emulsifiers were not recognized to enhance the transdermal penetration of pharmaceutical agents.

Preferably, when used as a rub-on lotion, the compositions of the present invention have a pleasing moisturizing lotion consistency. The compositions should preferably maintain an acceptable viscosity (e.g., at least about 4,000 centipoise) at ambient temperatures (i.e., 21–25° C.), and preferably up to about 35° C. Preferred compositions are stable to heat and cool cycles (heating up to 50° C. higher and cooling to ambient temperature) as well as freeze/thaw cycles (cooling to −30° C. and warming to ambient temperature). All of these attributes are affected by the types and amounts of emulsifiers chosen which comprise the emulsifier system of the present invention.

Also, surprisingly, the emulsifier system affects the penetration characteristics of the compositions. That is, it is believed that the emulsifier system in combination with a hydroalcoholic solvent system functions as a penetration enhancer by increasing the flux across the skin a pharmaceutical agent in the composition.

Suitable emulsifier systems should be compatible with the hydroalcoholic solvent system described above in order to provide suitable stability, acceptable properties, and appropriate viscosity. When used in devices requiring viscosification, compositions of this invention have a viscosity of at least about 4,000 centipoise (cps), preferably at least about 10,000 cps, more preferably at least about 20,000 cps, even more preferably at least about 50,000 cps, and most preferably at least about 150,000 cps (and even as high as about 500,000 cps or more), at 23° C., measured using a very low shear viscometer such as Brookfield LVDV-I+ viscometer and T spindles with a heliopath adapter.

Such viscosities can be obtained without the use of auxiliary thickeners, particularly conventional polymeric thickeners, although such polymers can be added to the compositions of the present invention in addition to the emulsifiers if so desired. Such polymeric thickeners are known to one of skill in the art. Because additional components such as additional penetration enhancers and emollients and other optional ingredients may affect the viscosity (either positively or negatively), the measured viscosity is that of the final composition, with all of these additional components but without any added auxiliary thickeners (e.g., polymeric thickeners or colloidal thickeners).

The viscosity of the present invention is imparted by an emulsifier system comprising at least one emulsifier, and preferably at least two emulsifiers, and more preferably at least two emulsifiers from different classes. In certain embodiments of the present invention, the emulsifier system can include only one commercially available emulsifier (which will typically be a mixture of emulsifiers).

In preferred embodiments, at least one of the emulsifiers is a solid at ambient temperature. Such solid emulsifiers typically include at least one long chain hydrocarbon group of at least 12 carbon atoms, preferably at least 16 carbon atoms, more preferably at least 18 carbon atoms, and most preferably at least 22 carbon atoms. For systems having a lower alcohol to water ratio in excess of about 50:50, the long chain hydrocarbon group preferably has at least 18 carbon atoms. In addition to providing viscosification at higher alcohols levels, the longer hydrocarbon chain length is believed to reduce the irritation potential of the compositions.

Many commercially available emulsifiers are actually comprised of a mixture of chain lengths. For example, the emulsifier behenyl alcohol as commercially supplied is actually a mixture of alcohols consisting of primarily C22 and C20 fractions but contain detectable levels of C24, C18, and C16 fractions. For this reason, unless otherwise specified (as above) the chain lengths specified herein refer to the number average chain length. For example, solid emulsifiers preferably include long chain hydrocarbon groups having a number average chain length of at least 14 carbon atoms, preferably at least 16 carbon atoms, more preferably at least 18 carbon atoms, and most preferably at least 22 carbon atoms.

Emulsifiers of this invention are comprised of molecules having hydrophilic (polar) and hydrophobic (non-polar) regions on the same molecule and conform to be general structure:

$(R)_a(L)_b$ wherein "R" represents a hydrophobic group, "L" represents a hydrophilic group, and "a" and "b" are independently 1 to 4.

In preferred embodiments of the present invention, "R" represents an alkyl group of at least 12 carbon atoms, preferably at least 16 carbon atoms, more preferably at least 18 carbon atoms, and most preferably at least 20 carbon atoms; an alkenyl group of at least 12 carbon atoms, preferably at least 16 carbon atoms, and more preferably at least 20 carbon atoms; or an araklyl or aralkenyl group of at least 14 carbon atoms, preferably at least 18 carbon atoms, and more preferably at least 20 carbon atoms. When the ratio of lower alcohol to water exceeds about 50:50 by weight, the alkyl group includes at least 16 carbon atoms. Above a ratio of about 60:40 alcohol to water, at least one emulsifier should have a hydrophobe chain ("R" in the above formula) length of at least 18 carbon atoms. In preferred embodiments R is unbranched.

In the above formula, "L" represents a hydrophilic group. For example, L can include an amide group having the structure —NHC(O)R''' or —C(O)NHR''' where R''' is hydrogen or an alkyl group of 1–10 carbon atoms optionally substituted in available positions by N, O, and S atoms; an ester group of short chain alcohols or acids (e.g., L=—C(O)OR' or —OC(O)R' where R' is C1–C4 branched or straight chain alkyl optionally substituted in available positions by hydroxyl groups); a polyglucoside group having 1–10 glucose units and more preferably 1–3 glucose units; a polyglycerol ester group having 1–15 glycerol units, preferably 2–12 glycerol units, and more preferably 3–10 glycerol units; a secondary amine group; a tertiary amine group; and a quaternary amine group.

"L" can also include an anionic group such as a sulfate, sulfonate, phosphate, phosphonate, or carboxylate group, or a zwitterionic group having the formula:

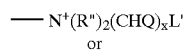

$$—N^+(R'')_2(CHQ)_xL'$$

or

-continued

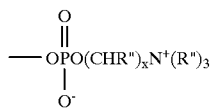

wherein each R" is independently hydrogen or an alkyl group (having 1–5 carbon atoms) or alkenyl group (having 2–4 carbon atoms), which alkyl or alkenyl groups are optionally substituted with nitrogen, oxygen, or sulfur atoms, including alkyl or alkenyl carboxyl groups; Q is hydrogen or hydroxyl; x is 1 to 4; and L' is —CO$_2^-$, —OP(O)(O$^-$)(O$^-$M$^+$), —(O)P(OR''')(O)(O$^-$M$^+$)(where R''' is hydrogen or an alkyl group of 1–10 carbon atoms optionally substituted in available positions by N, O, or S atoms), —SO$_2$O$^-$, or —OSO$_2$O$^-$, where M$^+$ is a positively charged counterion present in a molar ratio necessary to achieve a net neutral charge on the emulsifier and is selected from the group of hydrogen, sodium, potassium, lithium, ammonium, calcium, magnesium, or N$^+$R"$_4$.

"L" can also include an alcohol group; an ethylene oxide/propylene oxide copolymer group having 2–150 moles of ethylene oxide plus porpylene oxide per mole of hydrophobe ("R") and bonded to the hydrophobe through an ether or ester linkage, and optionally terminated by C1–C36 alkyl or C6 to C36 alkaryl ester; an ester or ether group of a polyhydric alcohol and their polyalkoxylated derivatives; an ester or ether of sorbitan or polyalkoxylated sorbitan group, as well as combinations of these groups, e.g., a polyethoxylated polyglucoside group. Thus, it will be understood by one of skill in the art that the emulsifiers can include combinations of all "L" hydrophilic groups described herein (e.g., ester groups and amide groups in one molecule).

The hydrophobic and hydrophilic groups of suitable emulsifiers, particularly non-ionic emulsifiers, are generally selected to yield an emulsifier system (i.e., one or more emulsifiers) having a weight average hydrophile/lipophile balance (HLB) of about 2 to about 20, more preferably about 4 to about 16, and most preferably about 6 to about 12. For example, an emulsifier system comprised of 40% by weight of an emulsifier with an HLB of 10 and 60% by weight of an emulsifier with an HLB of 15 has a weight average HLB of 13.

The emulsifiers in the emulsifier system used in the compositions of the present invention may be chosen from a single class of surfactants (e.g., a mixture of chain length alkyl polyglucosides), but is preferably a mixture of classes of surfactants. In systems with more than one emulsifier, each emulsifier is typically present in a concentration of at least about 0.05%, and more preferably at least about 0.1%, by weight to be considered a component of the emulsifier system. The total concentration of emulsifiers present as an emulsifier system is preferably at least about 0.5% by weight, based on the total weight of the composition of the present invention. The total concentration of emulsifiers present as an emulsifier system is generally less than about 30% by weight, preferably less than about 20% by weight, more preferably less than 10% by weight, and most preferably less than 5% by weight, based on the total weight of the composition of the present invention.

When compositions of the present invention ar substantially free of polymeric thickening agents (typically, those having a number average molecular weight of greater than 4000, often greater than about 20,000, and even in the hundreds of thousands), they have a "melt temperature" (T$_m$). If compositions are heated above this melt temperature, they dramatically lose (i.e., decrease) viscosity. The compositions of the present invention preferably have melt temperatures greater than about 25° C. in order to maintain a high viscosity (e.g., at least about 4000 centipoise) at ambient temperatures (i.e., 21–25° C.). In certain compositions, the melt temperature is greater than about 35° C. in order to generally maintain a high viscosity (e.g., at least about 4000 centipoise) once applied to the skin. It is recognized that a unique feature of many compositions of the present invention is the ability to melt when applied to skin. This dramatic loss in viscosity may be beneficial in some delivery devices. Some preferred compositions have a melt temperature greater than about 40° C. in order to allow shipping and handling without refrigeration.

The emulsifier systems affect the melt temperature of a given composition. For example, in order to obtain a melt temperature in excess of about 25° C. (and preferably, about 35° C.), the emulsifier system includes at least one emulsifier which is solid (e.g., a wax) at ambient temperature. However, having all emulsifiers of an emulsifier system solid at ambient temperature and/or choosing emulsifiers which individually have higher melting points will increase the melt temperature of the resultant composition most dramatically.

Also, the structure of emulsifiers in the emulsifier system affects the melt temperature of the resultant composition. In preferred embodiments, at least one emulsifier in the emulsifier system is capable of promoting a crystalline structure. Crystallinity is promoted by long straight chain alkyl groups. Therefore, at least one emulsifier preferably includes at least one saturated straight chain hydrocarbon group of at least 12 carbon atoms, preferably at least 14 carbon atoms, and more preferably at least 18 carbon atoms. The chain length may need to be even longer for systems having alcohol to water ratios of about 50:50 by weight or greater. Certain hydrophilic head groups have been found to particularly promote association and crystallization. Suitable crystalline emulsifiers include alkyl alcohols, alkyl polyglucosides, polyglycerol alkyl esters, C1–C4 esters of alkyl alcohols, C1–C4 esters of alkyl carboxylates, alkyl amides, alkyl betaines, and alkyl phosphates or phospholipids, alkyl quaternary amines, alkyl amine oxides, polyethoxylated alkyl alcohols, alkyl esters of polyethylene glycol, and mixtures thereof. Each of these compounds can be modified to include a variety of substituents as long as the compounds are crystalline.

In addition to effecting the melt temperature of a composition, the emulsifier chain length also helps to determine the maximum level of lower alcohol that can be used in the composition while maintaining a viscous composition (if so desired) and the concentration of emulsifiers required in the emulsifier system. For example, at higher levels of lower alcohol, longer chain emulsifiers are desired to produce stable viscous emulsions. It is believed that higher levels of lower alcohol tend to swell or solubilize the emulsifiers to a greater degree than lower levels of the same alcohol. Therefore, as the concentration of the lower alcohol increases, the chain length of the hydrocarbon group in the emulsifiers of the emulsifier system also increases in order to maintain a melt temperature over 25° C. (preferably, over 35° C.).

That is, the amount of lower alcohol in the hydroalcoholic system can affect the choice of surfactant, and vice versa. For example, if the composition includes a lower alcohol to water ratio in excess of about 50:50, the thickener system should include at least one surfactant having a number average chain length of at least 16 carbon atoms. If the composition includes a lower alcohol to water ratio in excess of about 60:40, the thickener system should include at least one surfactant having a number average chain length of at least 18 carbon atoms. If the composition includes a lower alcohol to water ratio in excess of about 64:36, the thickener system should include at least one surfactant having a number average chain length of at least 20 carbon atoms.

Specifically, systems based on a C16/C18 alkyl polyglucoside ("MONTANOV 68" available from Seppic, Inc. of Fairfield, N.J.) in combination with a C18 polyethoxylate ("BRIJ 76" available from ICI of Wilmington, Del.) in 68:32 ethanol:water have a melt temperature of approximately 35° C. Similar systems having C22 hydrocarbon chains have melt temperatures of 45° C. of higher. In addition, as the chain length of the hydrophobic component in the emulsifier system increases, the amount of emulsifier required to achieve a certain viscosity decreases. For example, the "MONTANOV 68" C16/C18 alkyl polyglucoside/"BRIJ 76" polyethoxylated C18 alcohol emulsifier system requires approximately 5% total emulsifier to achieve a lotion-type viscosity. A similar system based on C22 hydrophobes achieves such a viscosity at only about 2% total emulsifier.

The nature and size of hydrophilic head groups of emulsifiers are important and help to determine which emulsifier systems produce stable viscous systems. Certain combinations of emulsifiers will produce stable viscous emulsions. Without being bound by theory, it is believed that the size, charge, and degree of hydrogen bonding are important parameters to determine how emulsifiers interact.

Many preferred emulsifier systems are capable of producing viscoelastic compositions which are very stable. By varying the ratio of emulsifiers, the degree of elasticity can be adjusted from almost a purely viscous composition to a highly elastic and even stringy or gel like composition. Increasing the elasticity of the system imparts added stability to prevent complete phase separation of immiscible emollients or pharmaceutical agents. Addition of certain emulsifiers with at least two hydrophobic groups per molecule has been shown to limit the viscoelasticity while ensuring stable viscous compositions. A favored class of emulsifiers having multiple hydrophobic groups per molecule are quaternary ammonium salts conforming substantially to the following structure:

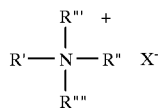

wherein: R' is a straight chain alkyl or alkenyl group of at least 12 carbon atoms, preferably at least 16 carbon atoms, more preferably at least 18 carbon atoms, and most preferably at least 20 carbon atoms; R''' is a short chain alkyl group of 1 to 4 carbon atoms, preferably methyl or ethyl; R'' is the same as R''', or is a long chain alkyl or alkenyl group of at least 12 carbon atoms, preferably at least 16 carbon atoms, more preferably at least 18 carbon atoms, and most preferably at least 20 carbon atoms, optionally substituted in available positions by N, O, or S atoms, or R'' is an aralkyl or aralkenyl group of at least 14 carbon atoms, preferably at least 18 carbon atoms, and more preferably at least 22 carbon atoms; R'''' is equivalent to either R'' or R''' and is preferably equivalent to R'''; and X is a halogen, R'''$SO_3^-$, R'''$SO_4^-$, R'''$CO_2^-$, (R''')$_2PO_4^-$, or (R''')$PO_4^=$. Some preferred structures include distearyldimethylammonium chloride, dibehenyldimethylammonium chloride, and dibehenyldimethylammonium methosulfate, while dibehenyldimethylammonium methosulfate is a more preferred structure. Other suitable multiple hydrophobic emulsifiers include dialkylglycerol esters, trialkylglycerol esters, polyglycerol alkyl esters, ethylene glycol dialkylesters, polyethylene glycol dialkylesters, dialkylamides of diamines such as ethylene diamine, polyalkylesters of pentaerythritol and dialkyl (optionally ethoxylated) phosphates, and alkyl esters of polyethyoxylated alkyl alcohols.

The following emulsifier classes are offered as nonlimiting examples of suitable emulsifiers for use in the present invention. Examples of some preferred emulsifiers are provided for each emulsifier class. For the present invention an emulsifier is preferably present with at least one coemulsifier to provide an emulsifier system to produce stable viscous compositions, although certain embodiments include only one emulsifier in the emulsifier system. The classes of emulsifiers are as follows.

Class 1. Alkyl or Alkenyl Polyglucosides:

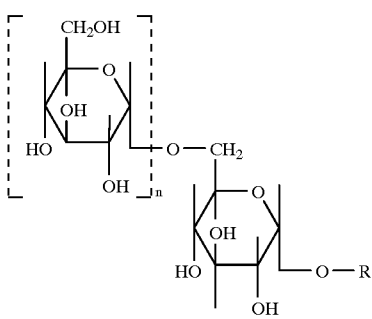

wherein R is a straight chain alkyl or alkenyl group of at least 12 carbon atoms, preferably at least 16 carbon atoms, more preferably at least 18 carbon atoms, and most preferably at least 20 carbon atoms; or an aralkyl or aralkenyl group of at least 14 carbon atoms, preferably at least 18 carbon atoms, and more preferably at least 22 carbon atoms; and n=0–10 (when n=0, the valence of the oxygen atom is completed by H), preferably 1–5, and more preferably 1–3.

Nonlimiting examples of preferred alkyl or alkenyl polyglucoside emulsifiers include cetearyl glucoside sold as "MONTANOV 68" by Seppic, Inc. of Fairfield, N.J.; Behenyl glucoside, produced experimentally as "ESSAI 624" MP, an alkyl polyglucoside prepared with 92% C-22 alcohol and corn-derived glucoside by Seppic, Inc.; and oleyl glucoside.

Class 2. Short Chain Esters of Long Chain Alcohols or Acids:

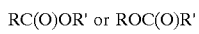

wherein R is as defined above for Emulsifier Class 1, and R' is a C1–C4 branched or straight chain alkyl group, optionally substituted in available positions by hydroxyl groups.

Some preferred short chain esters of long chain alcohols or acids include, but are not limited to, methyl behenate sold as "KEMESTER 9022" by Witco, Humko Chemical Divison of Memphis, Tenn.; methyl stearate sold as "KEMESTER 4516" by Witco; methyl oleate sold as "KEMESTER 205" by Witco; arachidyl propionate available as "WAXENOL 801" from Alzo of Sayreville, N.J.; behenyl lactate, stearyl acetate; and glycerol monoerucate available from Croda, Inc. of Parsippany, N.J.

Class 3. Alkyl and Alkenyl Alcohols:

$$R_6\text{—OH}$$

wherein $R_6$ is a straight or branched alkyl or alkenyl hydrocarbon chain of at least 12 carbon atoms, preferably at least 16 carbon atoms, more preferably at least 18 carbon atoms, and most preferably at least 20 carbon atoms, optionally substituted in available positions by N, O, or S atoms; or an aralkyl or aralkenyl group of at least 14 carbon atoms, preferably at least 18 carbon atoms, and more preferably at least 22 carbon atoms, optionally substituted in available positions by N, O, or S atoms.

Nonlimiting examples of preferred alkyl and alkenyl alcohol emulsifiers useful in an emulsifier system of the invention include stearyl alcohol available as "LANETTE 18" from Henkel's Emery Division of Cincinnati, Ohio; behenyl alcohol available as "LANETTE 22" from Henkel; oleyl alcohol available as "NOVOL" from Croda Inc.; C24 alcohol available as "UNILIN 350" from Petrolite of Tulsa, Okla.; C31 alcohol available as "UNILIN 425" from Petrolite; and arachidyl alcohol available as "AR-20" from M. Michel and Co. of New York, N.Y.

Class 4. Polyglycerol Ester:

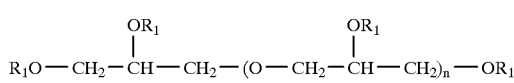

wherein each $R_1$ is independently hydrogen or a straight chain alkyl group of at least 12 carbon atoms, preferably at least 16 carbon atoms, more preferably at least 18 carbon atoms, and most preferably at least 20 carbon atoms; or an aralkyl or aralkenyl group of at least 14 carbon atoms, preferably at least 18 carbon atoms, and more preferably at least 22 carbon atoms; and n=0 to 15, preferably 1 to 12, and more preferably 2 to 10.

Some examples of preferred polyglycerol ester emulsifiers useful in a emulsifier system of the present invention include, but are not limited to, decaglycerol monostearate available as "POLYALDO 10-1-S" from Lonza Inc. of Fairlawn, N.J.; tetraglycerol monostearate available as "TETRAGLYN 1-S" from Barnet Products Corporation of Englewood Cliffs, N.J.; and decaglycerol tetrabehenate.

Class 5. Quaternary Amines:

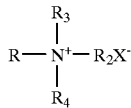

wherein R is as defined above for Emulisifer Class 1; $R_3$ is a short chain alkyl group of 1 to 4 carbon atoms, preferably methyl or ethyl; $R_2$ is the same as $R_3$, or is a long chain alkyl or alkenyl group of at least 12 carbon atoms, preferably at least 16 carbon atoms, more preferably at least 18 carbon atoms, and most preferably at least 20 carbon atoms, optionally substituted in available positions by N, O, or S atoms, or $R_2$ is an aralkyl or aralkenyl group of at least 14 carbon atoms, preferably at least 18 carbon atoms, and more preferably at least 22 carbon atoms; $R_4$ is equivalent to either $R_2$ or $R_3$ and is preferably equivalent to $R_3$; and X is a halogen, $R_5SO_3^-$, $R_5SO_4^-$, $R_5CO_2^-$, $(R_5)_2PO_4^-$, or $(R_5)PO_4^=$ (wherein $R_5$ is defined below in class 6).

Nonlimiting examples of quaternary amine emulsifiers include dibehenyldimethylammonium methosulfate available as "INCROQUAT DBM-90" from Croda; behenyltrimethylammonium chloride available as "NIKKOL CA-2580" from Barnet Products; and tallowtrimethylammonium chloride available as "ARQUAD T-27W" from Akszo Chemicals, Inc. of Chicago, Ill.

Class 6. Tertiary Amines and their Protonated Salts:

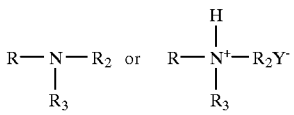

wherein R, $R_2$, and $R_3$ are as defined above for Emulsifier Class 5; additionally, $R_2$ and $R_3$ may be selected from polyethoxylated or polyproxylated alkyl or alkenyl alcohol chains having 1–50 moles of ethylene oxide or propylene oxide groups per mole of emulsifier; and Y is a halogen, $R_5SO_3^-$, $R_5SO_4^-$, $R_5CO_2^-$, $(R_5)_2PO_4^-$, or $(R_5)PO_4^=$, wherein $R_5$ is an alkyl or alkenyl group of 1–22 carbon atoms optionally substituted in available positions by N, O, or S atoms.

Some examples of emulsifiers from the class of tertiary amines and their protonated salts useful in the emulsifier system of the invention include, but are not limited to, behenamidopropyldimethylamine available as "INCROMINE BB" from Croda; behenamidopropyldimethylamine gluconate; tallowdimethylamine hydrochloride; dihydrogenated tallow methyl amine; stearyl diethanolamine hydrochloride; and polyethoxylated stearyl diethanolamine hydrochloride.

Class 7. Amine Oxides:

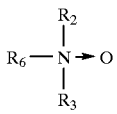

wherein $R_2$ and $R_3$ are as defined above for Emulsifier Class 6 and $R_6$ is as defined above for Emulsifier Class 3.

Nonlimiting examples of emulsifiers from the class of amine oxides suitable in the emulsifiers system of the invention include behenamine oxide (behenyldimethylamine oxide) available as "INCROMINE B-30P" from Croda; stearamine oxide available as "INCRAMINE OXIDE S" from Croda; behenamidopropyldimethyl amine oxide; and bis(2-hydroxyethyl)tallow amine oxide available as "AROMOX T/12" from Akzo.

Class 8. Polyethoxylated Alcohols and Esters and Derivatives Thereof:

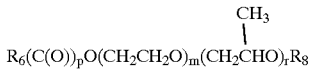

wherein $R_6$ is as defined above for Emulsifier Class 3; m=0–200, preferably 2–50, more preferably 4–20; p=0 or 1; $R_8$=H or —C(O)—$R_{12}$, wherein $R_{12}$ is an alkyl or alkenyl group of 1–36 carbon atoms optionally substituted by N, O, or S, or an aralkyl group of 6 to 36 carbon atoms; and r=0–50.

Emulsifiers from this particular class can be used alone (i.e., without a second emulsifier). Some examples of preferred emulsifiers from the class of polyethoxylated alcohols and esters, include but are not limited to, steareth-2 available as "BRIJ 72" from ICI Americas Inc. of Wilmington, Del. steareth-10 available as "BRIJ 76"from ICI; beheneth-5 available as "NIKKOL BB-5" from Barnet Products Inc.; beheneth-10 available as "NIKKOL BB-10" from Barnet; C31 alkyl-10EO available as "UNITHOX 450" from Petrolite Corp. of Tulsa, Okla.; C31 aklyl-40EO available as "UNITHOX 480" from Petrolite; and an example of a hydrophobe terminated polyethyoxylate is the lauric ester of "UNITHOX 480" available from Petrolite as "X-5171".

Class 9. Zwitterionics:

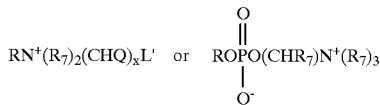

wherein R is as defined above for Emulsifier Class 1; each $R_7$ is independently hydrogen or an alkyl group (having 1–5 carbon atoms) or alkenyl group (having 2–4 carbon atoms), which alkyl or alkenyl groups are optionally substituted with nitrogen, oxygen, or sulfur atoms, including alkyl or alkenyl carboxyl groups; Q is hydrogen or hydroxyl; x is 1 to 4; and L' is $-CO_2^-$, $-OP(O)(O^-)(O^-M^+)$, $-(O)P(OR''')(O)(O^-M^+)$ (where R''' is hydrogen or an alkyl group of 1–10 carbon atoms optionally substituted in available positions by N, O, or S atoms), $-SO_2O^-$, or $-OSO_2O^-$, where $M^+$ is a positively charged counterion present in a molar ratio necessary to achieve a net neutral charge on the emulsifier and is selected from the group of hydrogen, sodium, potassium, lithium, ammonium, calcium, magnesium, or $N^+R'_4$ where each R' is independently an alkyl group of 1 to 4 carbon atoms optionally substituted with N, O, or S atoms.

Nonlimiting examples of emulsifiers from the class of zwitterions useful in the emulsifier system of the invention include stearamidopropylPG-dimmonium chloride phosphate available as "PHOSPHOLIPID SV" from Mona Industries of Paterson, N.J.; and behenyl betaine available as "INCRONAM B-40" from Croda.

Class 10. Alkyl and Alkenyl Amides:

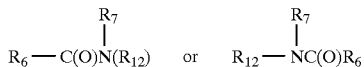

wherein $R_6$, $R_7$, and $R_{12}$ are as defined above for Emulsifier Classes 3, 9, and 8, respectively.

Examples of some preferred emulsifiers from the class of alkyl and alkenyl amides useful in the emulsifier system of the invention include, but are not limited to, behenamide available as "KEMAMIDE B" from Witco; behenamidopropyldimethyl amine available as "INCROMINE BB" from Croda; stearyldiethanolamide available as "LIPAMIDE S" from Lipo Chemcials Inc. of Paterson, N.J.; and Erucamide available as "ARMID E" from Akzo.

Class 11. Esters and Ethers of Polyhydric Alcohols:

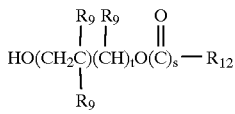

wherein t=0–4; each $R_9$ is independently chosen from H, $-CH_2OR_{10}$, $-OH$, or a hydrocarbon chain of 1 to 4 carbon atoms, preferably containing 1 carbon atom; s=0 or 1; wherein $R_{10}$=H or $R_{12}$ wherein $R_{12}$ is as defined above for Emulsifier Class 8.

Examples of esters and ethers include glycerol monobehenate, pentaerythritol distearate and glycerol tribe-henate. Esters and ethers of polyethoxylated polyhydric alcohols are also useful. For example, these include, but are not limited to, polyethoxylated glycerol monostearate, polyethoxylated penta erythritol behenate, and polyethoxylated propylene glycol monostearate.

Class 12. Anionics:

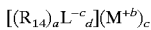

wherein $R_{14}$ is an alkyl, alkenyl, or aralkyl group of at least 12 carbon atoms, preferably at least 16 carbon atoms, more preferably at least 18 carbon atoms, and most preferably at least 20 carbon atoms, optionally comprising oxygen, nitrogen, or sulfur atoms within or substituted upon the alkyl or alkenyl chain; or a polyethoxylated and/or polypropoxylated alkyl, alkenyl, or aralkyl group, which alkyl, alkenyl, or aralkyl group comprises at least 14 carbon atoms, preferably at least 16 carbon atoms, more preferably at least 18 carbon atoms, and most preferably at least 20 carbon atoms, optionally comprising oxygen, nitrogen, or sulfur atoms within or substituted upon the alkyl, alkenyl, or aralkyl chain. When $R_{14}$ comprises a polyethoxylated or polypropoxylated substituent or a copolymeric substituent of ethylene oxide and propylene oxide, these subunits are present in amount of 1 to 100 moles, preferably 1 to 20 moles per mole of hydrophobe; L is sulfate ($-OSO_2O^-$), sulfonate ($-SO_2O^-$), phosphate (($-O)_2P(O)O^-$ or $-OP(O)(O^-)_2$), or carboxylate ($-CO_2^-$); M is hydrogen ($H^+$), sodium ($Na^+$), potassium ($K^+$), lithium ($Li^+$), ammonium ($NH_4^+$), calcium ($Ca^{+2}$), magnesium ($Mg^{+2}$), or $R''A^+$, wherein R'' is hydrogen or an alkyl or cycloalkyl group of about 1 to 10 carbon atoms, and $A^+$ is selected from the group consisting of $-N^+(R)_3$ (e.g., $R''A^+$ can be $N^+(CH_3R)_4$, $HN^+(CH_2CH_2OH)_3$, $H_2N^+(CH_2CH_2OH)_2$), or a heterocyclic $-N^+B$ wherein B comprises 3 to 7 atoms selected from the group consisting of carbon, nitrogen, sulfur and oxygen atoms which complete the nitrogen-containing heterocyclic ring and satisfy the valence on the nitrogen atom, and wherein R is the same as R'' and may also be substituted in available positions with oxygen, nitrogen or sulfur atoms; "a" and "c" are independently 1 or 2; "b" and "d" are independently 1,2 or 3; and "e" is equal to (c times d)/b.

Nonlimiting examples of preferred emulsifiers from the anionic class of emulsifiers suitable for use in the emulsifier system of the invention include behenic acid available as "CROACID B" from Croda, Inc.; stearyl phosphate available as "SIPPOSTAT 0018" from Specialty Industrial Products, Inc. of Spartanburg, S.C.; and sodium stearate available from Witco.

Class 13. Sorbitan Fatty Acid Esters

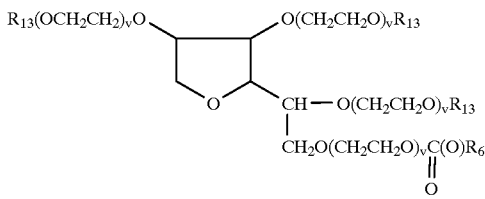

$R_{13}$ is H or $-C(O)R_6$ ($R_6$ is as defined above for Emulsifier Class 3), and each v is independently 0–30.

Fatty acid esters of sorbitan and its polyethoxylated derivatives, polyoxyethylene derivatives of mono- and polyfatty esters, are also examples of additional emulsifiers useful in the present invention.

Certain combinations of the above-listed emulsifiers are useful in some preferred embodiments to form viscous stable emulsifier systems of the present invention. These preferred systems are listed below.

Nonlimiting Examples of Suitable Emulsifier Systems

| System # | Emulsifier 1/(Class)* | | Emulsifier 2/(Class)* | | Emulsifier 3/(Class)* | | Emulsifier 4(Class)* | |
|---|---|---|---|---|---|---|---|---|
| 1 | alkyl polyglucoside | (1) | polyethoxylated alkyl alcohol | (8) | quaternary amine | (5) | | |
| 2 | alkyl polyglucoside | (1) | polyethoxylated alkyl alcohol | (8) | amine Oxide | (7) | | |
| 3 | alkyl polyglucoside | (1) | tertiary amine | (6) | | | | |
| 4 | alkyl polyglucoside | (1) | quaternary amine | (5) | | | | |
| 5 | polyglycerol ester | (4) | polyethoxylated alkyl alcohol | (8) | alkyl alcohol | (3) | | |
| 6 | polyglycerol ester | (4) | polyethoxylated alkyl alcohol | (8) | alkyl alcohol | (3) | alkyl ester | (2) |
| 7 | polyglycerol ester | (4) | polyethoxylated alkyl alcohol | (8) | quaternary amine | (5) | | |
| 8 | polyglycerol ester | (4) | alkyl ester | (2) | quaternary amine | (5) | | |
| 9 | polyglycerol ester | (4) | amine oxide | (7) | quaternary amine | (5) | | |
| 10 | alkyl/alkenyl alcohol | (3) | alkyl ester | (2) | quaternary amine | (5) | | |
| 11 | alkyl/alkenyl alcohol | (3) | alkyl ester | (2) | amine oxide | (7) | | |
| 12 | alkyl ester | (2) | polyethoxylated alkyl alcohol | (8) | quaternary amine | (5) | | |
| 13 | alkyl betaine | (7) | polyethoxylated alkyl alcohol | (8) | | | | |
| 14 | alkyl phospholipid | (9) | polyethoxylated alkyl alcohol | (8) | | | | |
| 15 | alkyl ester | (2) | alkyl alcohol | (3) | | | dialkoxydimethicone | |
| 16 | hydroxyfunctional ester | (2) | polyethoxylated alcohol | (8) | | | | |
| 17 | hydroxyfunctional ester | (2) | alkyl alcohol | (3) | quaternary amine | (5) | | |
| 18 | hydroxyfunctional ester | (2) | quaternary amine | (5) | | | | |
| 19 | polyglycerol ester | (4) | polyethoxylated alkyl alcohol | (8) | | | | |
| 20 | alkyl carboxylate | (12) | polyethoxylated alkyl alcohol | (8) | | | | |

*Refers to Emulsifier Classes identified above.
Alkyl/alkenyl alcohol     polyethoxylated alkyl alcohol It is a simple matter to test certain combinations of emulsifiers to determine if they provide a suitable stable emulsifier system. Screening methodology is set forth in the examples. The examples illustrate the importance of the head group size with respect to the ratio of the mixed emulsifiers in preferred emulsifier systems that produce a stable thickened emulsion. For example, systems based on a C16/C18 alkyl polyglucoside combined with C18 polyethoxylates of varying level of ethoxylation ("BRIJ") produce stable emulsions at widely varying ratios.

Without intending to be bound by theory, the physical structure of the composition of the invention is believed to be that of an emulsion. A classic definition of an emulsion is a stable dispersion of one liquid in a second imiscible liquid. However, as stated above, the present composition is preferably formed using at least one emulsifier which is a solid (e.g., a wax) at ambient temperature. The compositions of the present invention are believed to be a stable viscous mixture of a solid, semisolid, or liquid phase in a second liquid phase. It is believed that if certain hydrophobic emollients are added to the present invention, hydrophobic emulsifiers and immiscible emollients form an "oil" or hydrophobic phase which is dispersed in the hydroalcoholic liquid phase to form an "oil" in "water" emulsion. The hydroalcoholic phase is referred to herein as the "water" phase. Since many preferred emulsions are somewhat viscoelastic, these emulsions are believed to be liquid crystalline emulsions which have been cooled below the crystallization temperatures of the chosen emulsifiers to form a semi-crystalline gel-like network. Certain formulations may be simply swollen crystalline precipitates forming a strongly interacting network in the hydroalcoholic phase (so called coagel phase). The compositions of the present invention may also exist as combinations of these structures. Liquid crystalline and coagel phases in aqueous systems are described in "Application of Emulsion Stability Theories to Mobile and Semisolid O/W Emulsions," *Cosmetics and Toiletries*, Vol. 101, pp 73–92 (1986), and "Influence of Long Chain Alcohols (or Acids) and Surfactants on the Stability and Consistencies of Cosmetic Lotions and Creams," *Cosmetics and Toiletries*, Vol. 92, pp. 21–28 (1977). The exact type of molecular association that occurs depends on many factors, including the nature, size, and physical and chemical states of the polar and hydrocarbon portions of the emulsifiers which comprise the emulsifier system at a specified temperature.

Emulsifiers other than those required in the composition to provide the emulsifier system described herein may also function as penetration enhancers, emollients, or stabilizers. For example, certain emollients are also comprised of hydrophobic and hydrophilic regions and are useful in the present invention since they are believed to become incorporated into the liquid crystalline network. These emollients tend to enhance the stability of the composition as is discussed more fully below. Furthermore, certain dimethicone copolyol surfactants can actually improve the stability of formulations incorporating emollients. This is also discussed in more detail below.

Pharmaceutical Agents

Pharmaceutical agents (e.g., medicaments) suitable for use in compositions of the present invention are compounds that are intended to be delivered transdermally (i.e., through the skin into the circulatory system) to a mammal to alter biological function to treat, cure, and/or prevent disease or abnormal conditions.

Suitable pharmaceutical agents exhibit an optimal combination of such properties as water solubility, polarity, structure, and molecular weight. For instance, molecular weights are typically between about 100 daltons and about 5000 daltons, and preferably between about 200 daltons and about 1200 daltons.

Suitable pharmaceutical agents include antiinflammatory drugs, both steroidal (e.g., prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204, 219) antiulceratives such as H2 antagonists; steroidal hormones (e.g., progesterone, testosterone, estradiol, levonorgestrel); antivirals and/or immunomodulators (e.g., 1-isobutyl-1H-imidazo[4,5-c]quinolin-4amine, 1-(2-hydroxyl-2-methylpropyl)-1H-imidazo[4,5-c]quinoline-4-amine, acyclovir); cardiotonics (e.g., digitalis, digoxin); antitussives (e.g., codeine, dextromethorphan); antihistamine (e.g., diphenhydramine, chlorpheniramine, terfenadine); narcotic analgesics (e.g., morphine, fentanyl); peptide hormones (e.g., human or animal growth hormones LHRH); cardioactive products such as atriopeptides; proteinaceous products (e.g., insulin); enzymes (e.g., antiplague enzymes, lysozyme, dextranase), antinauseants (e.g., scopolamine); anticonvulsants (e.g., carbamazepine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatriptan); antiarrhythmic agents (e.g., flecainide); antiemetics (e.g., metoclopramide, ondansetron); anticancer agents (e.g., methotrexate); neurologic agents such as anxiolytic drugs; hemostatics; antiobesity agents; nicotine; and the like, as well as pharmaceutically acceptable salts and esters thereof.

The pharmaceutical agent is present in a transdermal delivery device of the invention in a therapeutically effective amount, i.e., an amount effective to bring about a desired therapeutic result in the treatment of a condition. The amount that constitutes a therapeutically effective amount varies according to the particular pharmaceutical agent incorporated in the device, the condition being treated, any pharmaceutical agent being coadministered with the selected pharmaceutical agent desired duration of treatment, the surface area of the skin over which the device is to be placed, the type of device being utilized, the choice of excipients, and other components of the device.

Transdermal Delivery Systems

The compositions of the present invention can be used in a variety of transdermal delivery systems (e.g., devices). A variety of such systems have been described. The simplest is a lotion of the pharmaceutical agent-containing hydroalcoholic composition of the present invention. When used as a lotion it is important to deliver efficacious and precise amounts since the composition contains a pharmaceutical agent. The compositions of the present invention can be dispensed in a discreet, substantially uniform amount using the dispensers disclosed in Applicants' Assignees' Copending U.S. patent application Ser. Nos. 08/668,198, filed Jun. 21, 1996, entitled "Dispenser for Antimicrobial Liquids" and 08/668,270, filed Jun. 21, 1996, entitled "Drip Resistant Nozzle for a Dispenser". Others include matrix devices in which the pharmaceutical agent-containing hydroalcoholic composition of the present invention is placed within a polymeric material such as a hydrogel layer or adhesive; reservoir devices in which the pharmaceutical agent-containing hydroalcoholic composition is delivered to the skin through a rate-controlling membrane; drug-in-adhesive devices in which the pharmaceutical agent-containing hydroalcoholic composition of the present invention is combined with an adhesive composition; and more complex multilaminate devices involving several distinct layers (e.g., layers for containing the pharmaceutical agent-containing hydroalcoholic composition, for containing excipients, for controlling the rate of release of the pharmaceutical agent and excipients, and for attaching the device to the skin). Each of these devices include an adhesive to maintain contact with the patient's skin and a backing that protects the device from external factors while in use, thereby forming a patch.

An exemplary reservoir device is shown in FIG. 1. Device 10 comprises a backing 12, a matrix 14 containing the composition of the present invention with the pharmaceutical agent therein, an optional membrane 15 (not shown) for controlling the rate at which the pharmaceutical agent is delivered to the skin, an adhesive layer 16, and a release liner 18.

Optional Ingredients

In addition to alcohol, water, the emulsifier system, and the pharmaceutical agent, the compositions of the present invention may optionally include ingredients such as penetration enhancers, salts, emollients, stabilizers, antimicrobials, fragrances, and propellants.

Penetration Enhancers

Additional compounds other than the lower alcohol or components of the emulsifier system may also be present in the composition to further boost the penetration of a particular pharmaceutical agent. These penetration enhancers may be present primarily in either the oil-like phase of the emulsion or the hydroalcoholic phase. Non-limiting examples of additional penetration enhancers include $C_8$–$C_{22}$ fatty acids such as isostearic acid, octanoic acid, and oleic acid; $C_8$–$C_{22}$ fatty alcohols such as oleyl alcohol and lauryl alcohol; lower alkyl esters of $C_8$–$C_{22}$ fatty acids such as ethyl oleate, isopropyl myristate, butyl stearate, and methyl laurate; di(lower)alkyl esters of $C_6$–$C_8$ diacids such as diisopropyl adipate; monoglycerides of $C_8$–$C_{22}$ fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Certain emulsifier systems may also significantly increase the flux of particular pharmaceutical agents. This may be particularly true of emulsifiers that are in a pure state liquids at skin temperature such as those having shorter chain hydrophobes (e.g., methyl laurate), unsaturated hydrophobes (methyl oleate, oleic acid, oleyl alcohol, glycerol monooleate), and branched hydrophobic hydrocarbon chains (isostearyl alcohol).

Salts

The melt temperature of the compositions of the present invention may be increased by adding salts. Salt addition may also effect the stability as well as penetration rate of certain pharmaceutical agents. As the concentration of salt is increased, the ratio of emulsifiers will often need to change in order to maintain a stable composition. It is important to choose salts that do not create an unstable system and are compatible with the pharmaceutical agents present in the system. For example, certain quaternary compounds may precipitate rapidly in the presence of halide salts. Therefore, if a system includes ionic compounds, a salt is preferably selected that is compatible with the pharmaceutical agent and emulsifier system. For example, choosing a salt with the same or similar counterion may work well.

Stabilizers

A stable composition is one that does not separate more than 10% by volume after centrifuging 17 mm O.D.×119 mm long at 1545×g for 30 minutes as measured at the longitudinal midpoint of a 15 ml centrifuge tube. It is also recognized that stability may be time dependent due to crystallization of emulsifiers and/or emollients present in the system, coalescence of emollients, emulsifiers and the like. Therefore, preferred compositions do not exhibit separation of more than 10% after standing for 6 months at ambient conditions.

Two types of stabilizers are useful in the present invention. These include (1) those stabilizers that complex with emulsifier hydrophilic head groups, and (2) those that associate with the emulsifier hydrophobic tails. Certain stabilizers may perform both functions. For example, emulsifiers comprising 1,2 diol-containing head groups such as alkylpolyglucosides, monoalkylglycerides, and polyglycerol alkyl esters, may be "stabilized" by adding borate ion. Without intending to be bound by theory, it is believed that borate ions complex with adjacent head groups which may increase the association of hydrophobic tails by holding them in close proximity. Natural or synthetic polymers comprised of pendent long chain alkyl groups (greater than 12 and preferably greater than 16 carbon atoms), such as stearyl modified cellulose derivatives, stearyl modified proteins such as wheat protein, stearyl modified collagen, and the like, are capable of stabilizing compositions of the present invention. Such added components may also increase the melt temperature of compositions of the present invention. It is believed that the pendent alkyl groups in these polymers associate by Van der Waals interactions with the hydrophobes of an emulsifying system, thereby enhancing the stability of the crystalline structure.

Polymeric thickeners that do not have associative pendent alkyl chains may also increase the melt temperature presumably by increasing the viscosity of the continuous phase. A nonlimiting example of such thickeners are quaternary celluloses such as "CELQUAT 230M" as available from National Starch of Bridgewater, N.J. In preferred embodiments, stearyldimonium hydroxypropyl cellulose commercially available as "CRODACEL QS" from Croda Inc., Parsippany, N.J. is added as a stabilizer.

Emollients

Emollients may be added to the compositions to encourage good skin health. Emollients are generally separated into two broad classes based on their function. The first class of emollients function by forming an occlusive barrier to prevent water evaporation from the stratum corneum. The second class of emollients penetrate into the stratum corneum and physically bind water to prevent evaporation. The first class of emollients is subdivided into compounds that are waxes at room temperature and compounds which are liquid oils. The second class of emollients includes those that are water soluble and are often referred to as humectants.

For the purpose of this invention the emulsifier system is considered separate and distinct from any emollients which may be added even though it is recognized that the emulsifiers may function as occlusive emollients and aid in maintaining or improving the skin condition. If emollients are included, they preferably comprise about 0.5% to about 30%, more preferably about 2% to about 20%, and most preferably about 4% to about 16%, by weight of the formulation.

For compositions which may be rubbed on the skin the cosmetic feel of the product is important. For these embodiments the ratio of wax to liquid emollients (oils and humectants) in a preferred embodiment of this invention is within a range of about 5:1 to 1:5, and more preferably within a range of about 1:3 to about 3:1. Emollients may be selected from any of the classes known in the art. A general list of useful emollients appears in U.S. Pat. No. 4,478,853 (Chaussee), EPO Patent Publication No. 0 522 624 A1 (Dunphy et al.), and in the *CTFA Cosmetic Ingredient Handbook* published by The Cosmetic, Toiletry, and Fragrance Association, Wash. D.C. (1992) under the listings "Skin Conditioning agents," "emollients," "humectants," "miscellaneous" and "occlusive."

In preferred emollient-containing embodiments, emollients are chosen from the following nonlimiting list of general emollients, occlusive emollients, and humectants. Examples of general emollients include short chain alkyl or aryl esters (C1–C6) of long chain (straight or branched) alkyl or alkenyl alcohols or acids (C8–C36) and their polyethoxylated derivatives; short chain alkyl or aryl esters (C1–C6) of C4–C12 diacids or diols, optionally substituted in available positions by —OH; alkyl or aryl C1–C9 esters of glycerol, pentaerythritol, ethylene glycol, propylene glycol, as well as polyethoxylated derivatives of these, and polyethylene glycol; C12–C22 alkyl esters or ethers of polypropylene glycol; C12–C22 alkyl esters or ethers of polypropylene glycol/polyethylene glycol copolymer; and polyether polysiloxane copolymers. In addition to many of the emulsifiers of preferred emulsifier systems, additional examples of occlusive emollients include cyclic dimethicones, polydialkylsiloxanes, polyaryl/alkylsiloxanes, long chain (C8–C36) alkyl and alkenyl esters of long straight or branched chain alkyl or alkenyl alcohols or acids; long chain (C8–C36) alkyl and alkenyl amides of long straight or branched chain (C8–C36) alkyl or alkenyl amines or acids; hydrocarbons including straight and branched chain alkanes and alkenes such as squalene, squalane, and mineral oil; polysiloxane polyalkylene copolymers, dialkoxy dimethyl polysiloxanes, short chain alkyl or aryl esters (C1–C6) of C12–C22 diacids or diols, optionally substituted in available positions by OH; and C12–C22 alkyl and alkenyl alcohols. Nonlimiting examples of preferred humectant type emollients include glycerol, propylene glycol, dipropylene glycol, polypropylene glycol, polyethylene glycol, sorbitol, pantothenol, gluconic acid salts, and the like.

Although an emulsifier system is responsible for the stability and overall consistency of compositions of the present invention, emollients may also affect the viscosity, stability, and melt temperature of a composition. It is anticipated that a single emollient, or two or more emollients, may be added to the compositions of the present invention. A wide range of emollients may be added to the compositions of the present invention. For rub-in compositions, preferably wax and oil type emollients along with water-soluble emollients are used. In a preferred rub-in embodiment, emollient systems are comprised of humectants in addition to occlusive wax and oil emollients in concentrations that achieve a moisturizing, but not greasy, composition, which maintains and improves the condition of the skin upon repeated use. Ideally, emollients are non-comedogenic and are chosen to ensure no skin irritation or sensitization reaction occurs. This is particularly critical since the compositions of the present invention may be present on the skin in an occluded device such as a reservoir patch. Furthermore, emollients should be chosen which do not affect the integrity of the device material. For example, many hydrophobic emollients such as mineral oil, petrolatum, and certain esters can act as plasticizers for polymeric and adhesive components.

Without being bound or limited by theory, it is believed that pharmaceutical agents and emollients (if added) in the present compositions may be present in four distinct regions. They could occur (1) as a soluble species in the solvent phase, (2) dispersed as emulsified droplets within the mixed emulsifier micelle or crystalline gel network, (3) incorporated into the mixed emulsifier micelle or crystalline gel network, or (4) as a separate and distinct emulsion. As stated above, emollients and/or pharmaceutical agents can affect the melt temperature of a composition. Those emollients and/or pharmaceutical agents that are soluble or dispersible in the solvent phase tend to have little or no affect on the melt temperature and are therefore preferred. These emollients include the humectant and general emollients. For systems requiring a high melt temperature, the most preferred general emollients are those which are essentially insoluble in water but soluble in the hydroalcoholic solvent. These emollients are also preferred since they remain soluble and uniformly dispersed even above the melt temperature, so that upon cooling to room temperature a uniform composition results. Such general emollients typically do not have alkyl or alkenyl chains greater than about 14, preferably not greater than 12, and most preferably not greater than about 9 carbon atoms.

Those pharmaceutical agents and/or emollients that are insoluble in the hydroalcoholic solvent may associate with the emulsifiers of the emulsifier system and/or become incorporated into the micelle or crystalline gel network. For systems requiring a high melt temperature preferred emollients within this class are those emollients that are very hydrophobic. For example, hexadecane can increase the viscoelasticity of certain emulsifier systems. Those emollients that are capable of associating with and disrupting the emulsifiers of the emulsifier system tend to decrease the melt temperature and may influence the stability of the composition. Certain branch alkyl esters of greater than about 12 carbon atoms per hydrophobe have been found to be particularly effective at decreasing the melt temperature. For example, trioctyldodecyl citrate has been found to significantly decrease the melt temperature of some systems.

Emollients that become incorporated into the emulsifier system tend to decrease the melt temperature. For example, laureth-4 ("BRIJ 30") appears to incorporate into the emulsifier system; it does not phase out (i.e., phase separate) when heated above the melt temperature at concentrations below about 1% by weight. Laureth-4 also tends to decrease the melt temperature of the composition.

Certain emollients that are insoluble in the hydroalcoholic solvent can be emulsified in what is believed to be a separate and distinct emulsion. These emollients have little affect on the melt temperature of a composition. For example, certain cyclic silicones, polysiloxanes, and dialkoxypolysiloxanes can be emulsified in hydroalcoholic solvents using polyether/polysiloxane copolymer surfactants. Cyclic silicones, such as "DC344" (available from Dow Corning of Midland, Mich.), in the presence of certain polyether/polysiloxane copolymers, such as "ABIL B88183" available from Goldschmidt Chemical Corp. of Hopewell, Va., can form a thermally stable emulsion such that the compositions remain uniform both above and below the melt temperature. In fact, the combination of a long chain dialkoxypolysiloxane and polyether/polysiloxane copolymer has been found to actually promote the stability of certain emulsifier systems. The dialkoxypolysiloxane is believed to interact with the emulsifier system as well as the polyether/polysiloxane copolymer. These compounds have the following structures. Dialkoxy Dimethicones:

R—O—Si(CH$_3$)$_2$—O[Si(CH$_3$)$_2$—O]$_z$—Si(CH$_3$)$_2$—OR wherein R is a straight chain alkyl group of 12–50 carbon atoms, preferably 16–24 carbon atoms, and z=5–300.

Polyether/Polysiloxane Copolymers (Dimethicone Copolyols):

(CH$_3$)$_3$—Si—O—[Si(CH$_3$)R$_{11}$—O]$_x$[Si(CH$_3$)R$_8$—O]$_y$—Si(CH$_3$)$_3$ wherein x+y=5–400, and preferably 15–200; R$_8$ is a polyether substituted alkyl group with the structure:

—R$_9$—O(C$_2$H$_4$O)$_p$(C$_3$H$_6$O)$_q$R$_{10}$ wherein p=2–300, and preferably 8–100; q=0–100; R$_9$ is an alkyl group of 1 to 6 carbon atoms; R$_{10}$ is hydrogen or an alky group of 1–22 carbon atoms; and R$_{11}$ is an alkyl group of 1 to 22 carbon atoms or phenyl.

Note that branched chain polysiloxanes modified as shown in the two structures above are also possible.

The following are nonlimiting examples of emulsifier/emollient components which improve thickening/stability of compositions of the present invention.

a. Certain wax emulsifiers/emollients have been found to be particularly useful and include solid waxy esters such as: Myristyl Myristate, Cetyl Palmitate, Myristyl Stearate, Stearyl Behenate, Behenyl Isostearate, Isostearyl Behenate, Behenyl Behenate, Lauryl Behenate, Behenyl Erucate. These have the following formula: R$_1$—CO$_2$—R$_2$ wherein: R$_1$ is an alkyl or alkenyl group of at least 14 carbon atoms; and R$_2$ is an alkyl or alkenyl group of at least 4 carbon atoms.

b. Long chain hydrocarbon di-esters or tri-esters of polyhydric alcohols with a melting point of greater than 23° C., including solid esters such as glycerol tribehenate and sorbitan tristearate.

c. Pure lanolins and lanolin derivatives (e.g., hydrogenated lanolin), which provide excellent emolliency but can also improve the stability of the emulsion when used in combination with oil emollients.

d. Petrolatums, which are mixtures of oily and waxy long chain hydrocarbons, provide excellent emolliency, and can also improve the stability of the emulsion when used in combination with oil emollients.

e. Microcrystalline waxes and branched hydrocarbon waxes with a melting point of greater than 50° C. and a molecular weight of greater than 400. Examples of this includes, but is not limited to, "VYBAR 103" branched hydrocarbon with a number average molecular weight of 2800, and "ULTRAFLEX" microcrystalline wax, both of which are available from Petrolite Corp. of Tulsa, Okla.

f. Oxidized waxes and modified hydrocarbon waxes, which are prepared from waxes modified by oxidation, salts of oxidized waxes, maleic anhydride adducts of polyolefins and urethane derivatives of oxidized synthetic or petroleum waxes. Applicable waxes could include Petrolite's Cardis or Petronauba microcrystalline and polyethylene-based oxidized products, Polymekon (salts) and Ceramer (anhydride adducts).

g. Fully saturated homopolymers of polyethylene, or copolymers of various alkene monomers having a molecular weight at or below 3,000 with a melting point below 130° C. and low melt viscosities. Applicable waxes could include "POLYWAX" available from Petrolite Corp.

Fragrances

The compositions of the present invention may also comprise a fragrance. If fragrances are included the fragrances must be chosen carefully since some fragrances are known to cause skin irritation and/or sensitization reactions.

Antimicrobials

In addition to the lower alcohols present in the composition of the present invention, other antimicrobials may be added to enhance the antimicrobial action of the compositions of the present invention. Suitable additional antimicrobials include iodine and its complexed forms such as povidone/iodine, chlorhexidine salts such as chlorhexidine digluconate (CHG), parachlorometaxylenol (PCMX), hexachlorophene, phenols, surfactants comprising a long chain hydrophobe (C12–C22) and a quaternary group, triclosan, "LAURICIDIN" glyceryl monolaurate, quaternary silanes, hydrogen peroxide, phenols, silver, silver salts such as silver chloride, silver oxide and silver sulfadiazine and the like. In order to reduce chances for irritation and yet maintain efficacy, the antimicrobial level should be adjusted to the minimum level which maintains a low bacteriological count for 6 and most preferably for 12 hours after application.

The most preferred additional antimicrobial is chlorhexidine because it is capable of ensuring long term antimicrobial efficacy. If chlorhexidine is added to the present invention it is preferably present as a soluble salt. The diacetate and digluconate salts are preferred. The most preferred antimicrobial is chlorhexidine digluconate (CHG). CHG is preferably present at a concentration of about 0.05–5.0%, more preferably about 0.1–3%, and most preferably about 0.25–2%, by weight based on the total weight of the composition. Chlorhexidine is a bis(diguanide) and therefore is very basic and is capable of forming multiple ionic bonds with anionic materials. For this reason, chlorhexidine-containing thickener system are preferably based on non-precipitating emulsifiers and polymers. These include certain alkyl phosphate and alkyl sarcosinate emulsifiers in combination with aminofunctional polymers. In addition, certain zwitterionic and cationic non-precipitating emulsifiers may also be useful.

Propellants

The composition of the present invention may also be formulated into an aerosol foam or mousse by addition of an appropriate propellant. The propellant must be chosen to ensure proper delivery from the container to prevent clogging of the valve. The propellant can be chosen from chlorofluorocarbons (CFCs), hydrochlorofluorocarbons (HCFCs), hydrofluorocarbons (HFCs), perfluorinated alkanes, and lower alkanes (C1–C5) as well as nitrous oxide, dimethyl ether, and other solvent-soluble propellants. Preferred propellants are lower alkanes such as propane, butane, and isobutane since these result in a dramatic loss in viscosity making the formulation easy to dispense. A 70:30 mixture of propane/isobutane is a particularly preferred embodiment. In order to produce an aerosol composition the antimicrobial lotion is first formulated and charged into an appropriate pressure rated container. If convenient, the formulation may be heated above the melt temperature in order to facilitate filling. The propellant is then added under pressure at approximately 2–30% preferably 3–20% by volume. The propellant may form a separate layer or may remain emulsified in the composition.

Methods of Preparation

The compositions of the present invention may be prepared by a variety of techniques. For example, the process can often be as simple as adding the emulsifier system to the hydroalcoholic solvent at a temperature above the melting point of the emulsifiers, mixing briefly and cooling, although the heating step may not be required. Either way, to ensure a composition of high stability, the components are preferably subjected to high shear (e.g., homogenized) for a limited time period. Preferably, the homogenization occurs while above the melting point of the emulsifier system followed by low shear mixing or no mixing at all while cooling. The system should be mixed under high shear long enough to ensure a very small "droplet" size, however, excessive high shear mixing may result in decreased viscosity and stability.

The cooling rate may be important depending on the particular emulsifier system. Certain emulsifier systems can be homogenized and then allowed to cool slowly, however, rapid cooling appears beneficial for most systems.

The order of adding the components may also affect the stability and viscosity of the system. In general, it works well to melt the mixed emulsifiers with aqueous-insoluble emollients together in one vessel. The hydroalcoholic solvent and any aqueous miscible emollients are mixed in a second vessel. Both components are heated above the melting temperature of the emulsifier system. The hot liquid components are mixed together rapidly followed by approximately 1 to 5 minutes of homogenization for typical batches under 500 grams. While still low in viscosity the system is stirred using moderate agitation and cooled. It is also possible to add the molten emulsifier system along with any solvent insoluble emollients to hot water (i.e., water at a temperature above the melting temperature) followed by high shear mixing and subsequent dilution with alcohol. In a particularly preferred method, the alcohol is added after cooling the aqueous emulsion to below about 30° C. The processing variables, including amount and intensity of high shear mixing, rate of cooling, and order of addition, are easily determined by one skilled in the art.

The pharmaceutical agent(s) may be added to the emulsifier phase, the aqueous or hydroalcoholic phase or may be added to the hydroalcoholic emulsion. If added to the hydroalcoholic emulsion, the pharmaceutical agent may be added above or below the melt temperature of the emulsifier system. In a preferred method the pharmaceutical agent is added after the system has cooled. However, if the pharmaceutical agent is only oil-soluble, it may be necessary to place it with the emulsifier and/or solvent and heat the combination.

TEST METHODS

Viscosity

In the following Examples (except where indicated) viscosity was measured at 23° C. at ambient pressure using a Brookfield LVDV-I+ viscometer equipped with a model D Brookfield heliopath and T spindles B-F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20–80% of the viscometer range and more preferably between 30–70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The following table outlines preferred spindles for various sample viscosities.

| Sample Viscosity | T Spindle to Use |
| --- | --- |
| 1,000–100,000 | B |
| 10,000–200,000 | C |
| 50,000–500,000 | D |

-continued

| Sample Viscosity | T Spindle to Use |
|---|---|
| 100,000–1,250,000 | E |
| 500,000–3,000,000 | F |

The viscosity of each sample was taken as the highest relatively stable reading achieved on the first path the spindle traversed using the heliopath adapter.

Stability

The stability of samples was measured 24 hours after conditioning at ambient conditions by placing 12 ml of a formulation that formed a lotion/cream in a 17 mm O.D.× 119 mm long 15 ml graduated centrifuge tube. The tube was then centrifuged in a Labofuge B (Heraeus Sepatech GmbH, Model 2650, rotor 2150 and buckets #2101) at 3000 rpm (1545×g when measured at the longitudinal midpoint of the sample tube) for 30 minutes at 23° C. Stability is recorded as a volume percent separation in the Examples below.

Melt Temperature

The melt temperature was measured by placing approximately 15 grams sample in a 25 cc sealed glass vial and placing the vial in a water bath. The temperature of the bath was increased periodically in discrete increments and the contents checked after approximately 1 hour at a given temperature. The melt temperature was taken as the temperature at which the mixture became very low in viscosity.

Cumulative Flux Test Method

Figure 2:
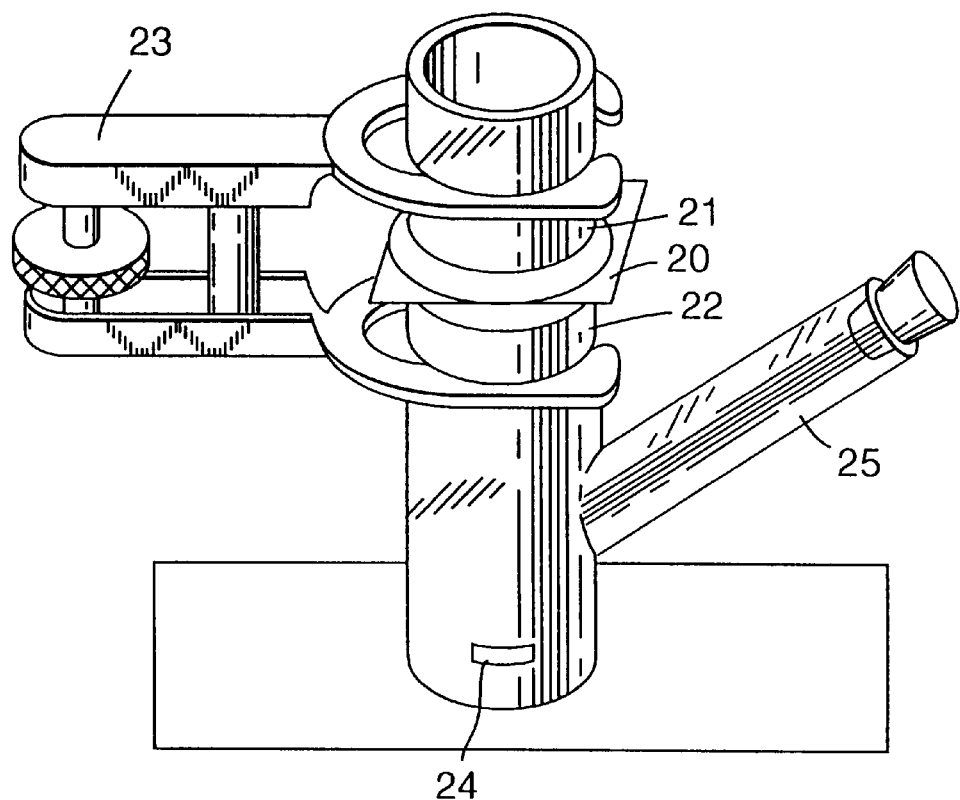
FIG. 2 is a perspective view of a diffusion cell for measuring transdermal penetration.

In the specific test procedure used herein, human cadaver skin was used with a vertical diffusion cell modeled after those described in the literature (e.g., Cohen et al., *J. Invest. Derm.*, 62, 507 (1974) and Stoughton, *Arch. Derm.*, 99, 753 (1964)). As shown in FIG. 2, the human skin 20 was mounted epidermal side up between the upper and lower portions of the cell 21 and 22 held together by means of a ball joint clamp 23. The cell below the skin was filled with 30% N-methyl-2-pyrrolidone in water to act as the "acceptor" fluid, thus maintaining an adequate "sink" receptor. The acceptor fluid was stirred using a magnetic stirring bar 24 and a magnetic stirrer (not illustrated). The sampling port 25 was stoppered except when in use.

A known amount of a composition to be evaluated was applied to the epidermal (upper) side of the skin in a uniform layer. The cell was then placed in a constant temperature (31–33° C.), constant humidity chamber (generally maintained at a humidity of about 40–50%) and kept there throughout the experiment. The chamber utilized a heat exchanger coupled to a constant temperature bath, with a fan to circulate air. A saturated calcium nitrate solution was used to maintain the humidity. The acceptor fluid was stirred by means of a magnetic stirring bar throughout the experiment to assure a uniform sample and a reduced aqueous diffusion layer on the dermal side of the skin. The acceptor fluid was removed at specified time intervals and fresh fluid was immediately added to replace the withdrawn fluid. The withdrawn aliquots were analyzed for pharmaceutical agent content by conventional high pressure liquid chromatography and the cumulative amount of the pharmaceutical agent was determined.

EXAMPLES

The following Examples are provided to illustrate the invention and are not intended to limit the scope of the invention.

Example 1

Transdermal Delivery of Testosterone in an Alkyl Polyglucoside/Polyethoxylated Alcohol Delivery Emulsifier System An alkyl polyglucoside emulsifier having an alkyl chain of 16 to 18 carbons was obtained as "MONTANOV 68" from Seppic Inc. of Fairfield, N.J. This highly crystalline emulsifier was combined with steareth-10 ("Brij 76" from ICI Chemicals) at various ratios in an ethanol/water solvent system as shown in the table below:

| | Formula No. | | | | | |
|---|---|---|---|---|---|---|
| | A | B | C | D | E | F |
| Component | | | [weight (g)] | | | |
| "MONTANOV 68" | 1.5 | 1.17 | 1.33 | 1.00 | 1.5 | 1.33 |
| "BRIJ 76" | 1.5 | 1.17 | 1.33 | 1.50 | 1.5 | 1.33 |
| Ethanol | 15 | 15 | 25.7 | 36.3 | 36.0 | 46.7 |
| Water | 82 | 82.7 | 71.7 | 61.3 | 61.0 | 50.7 |

Each composition was prepared using the following procedure:

1. The emulsifiers were heated above the melting temperature to 75° C.

2. The hydroalcoholic solvent was heated to 75° C. in a sealed jar.

3. The hot hydroalcoholic solvent was rapidly added to the molten emulsifiers.

4. The mixture was homogenized at maximum speed for 4 minutes using a Silverson L4R homogenizer available from Silverson Machines, Waterside England.

5. The vessel was then immersed in 15–20° C. water with moderate agitation using an overhead paddle impeller for 20 minutes.

All formulations produced stable viscous emulsions. The resultant viscosity shown in the table below was measured according to the viscosity test method described above. Several days after cooling, testosterone was added by dispersing excess testosterone (Sigma Chemical, St. Louis, Mo.) in each composition with mild sonication in an ultrasonic bath to a concentration of about 30 mg/ml. The compositions were then tested according to the Penetration Flux Test Method described above. The results are shown in the table below:

| Formulation | $T_m$ (° C.) | Viscosity (cps) | Cumulative Flux at 24 hours (microgram/cm$^2$) |
|---|---|---|---|
| A | >39 | 53000 | 56 |
| B | >39 | 31000 | 53 |
| C | >39 | 62000 | 58 |
| D | 38 | 31000 | 71 |
| E | 39 | 58000 | 90 |
| F | 35 | 36000 | 174 |

If testosterone were applied out of an aqueous vehicle without the use of any penetration enhancement (e.g., emulsifiers, penetration enhancers, etc.) a flux is estimated to be 0.3–2.4 micrograms/cm$^2$/24 hours. The results indicate that a significantly higher flux can be achieved using the hydroalcoholic emulsions of this invention. Note that the higher ethanol level of formula F produced a dramatic rise in the flux rates. Even higher levels of alcohol would be expected to produce even higher flux rates. A portion of formula F was applied to intact skin of a human volunteer and occluded using an open cellular foam carrier with an impervious backing with a peripheral ring of adhesive. After 24 hours only mild redness occurred. This indicates that these formulations provided a low irritation composition that have very good penetration enhancement.

Example 2

Transdermal Delivery of Testosterone in an Alkyl Alcohol/Polyethoxylated Alcohol Delivery Emulsion System Steareth-10 ("BRIJ-76" from ICI Chemicals) was combined with stearyl alcohol at various ratios in an ethanol/water solvent system as shown in the table below:

| | Formula No. | | | | | |
|---|---|---|---|---|---|---|
| | A | B | C | D | E | F |
| Component | [weight (g)] | | | | | |
| Stearyl alcohol | 0.5 | 1.5 | 0.83 | 1.33 | 0.5 | 1.5 |
| Steareth-10 | 1.5 | 0.5 | 1.33 | 0.83 | 1.5 | 0.5 |
| Ethanol | 15 | 15 | 25.7 | 25.7 | 36.5 | 36.31 |
| Water | 83 | 83 | 72.2 | 72.2 | 61.5 | 61.3 |

The emulsions were prepared according to the procedure of Example 1. All formulations produced stable viscous emulsions. The resultant viscosity shown in the table below was measured according to the viscosity test method previously described. Several days after cooling testosterone was added as described in Example 1 to a concentration of about 30 mg/ml. The compositions were then tested according to the Penetration Flux Test Method described above. The results are shown in the table below:

| Formulation | $T_m$ (° C.) | Viscosity (cps) | Cumulative Flux at 24 hours (microgram/cm$^2$) |
|---|---|---|---|
| A | 42–43 | 31000 | 44 |
| B | 42–43 | 290000 | 59 |
| C | 42–43 | 59000 | 73 |
| D | 42–43 | 97000 | 111 |
| E | 41 | 12000 | 89 |
| F | 42–43 | 17000 | 60 |

If testosterone were applied out of an aqueous vehicle without the use of any penetration enhancement a flux is estimated to be 0.3–2.4 micrograms/cm$^2$/24 hours. The results indicate that a significantly higher flux can be achieved using the hydroalcoholic emulsions of this invention. A portion of formula C was applied to intact skin of a human volunteer and occluded using an open cellular foam carrier with an impervious backing with a peripheral ring of adhesive. After 24 hours only mild redness occurred. This indicates that these formulations provided a low irritation composition that have very good penetration enhancement.

While in accordance with the patent statues, description of the preferred weight fractions, processing conditions, and product usages have been provided, the scope of the invention is not intended to be limited thereto or thereby. Various modifications and alterations of the present invention will be apparent to those skilled in the art without departing from the scope and spirit of the present invention. The Examples described in this application are illustrative of the possibilities of varying the type, quantity and ratio of components as well as the method for making compositions of the present invention. All patents, patent applications, and publications cited herein are incorporated by reference in their entirety, as if individually incorporated.

What is claimed is:

1. A hydroalcoholic composition useful for the enhancement of the transdermal delivery of a pharmaceutical agent through the skin and into the circulatory system of a patient, the composition comprising:

(a) a lower alcohol, which is a C1–C4 alcohol, and water in a weight ratio of at least about 20:80;
   (b) a pharmaceutical agent; and
   (c) an emulsifier system comprising at least two emulsifiers, each emulsifier being present in an amount of at least about 0.05% by weight, based on the total weight of the composition; wherein each emulsifier:
      (i) is of the formula $(R)_a(L)_b$ wherein "R" represents a hydrophobic group, "L" represents a hydrophilic group, and "a" and "b" are independently 1–4; and
      (ii) is selected such that the composition, when free of auxiliary thickeners, has a viscosity of at least about 4,000 centipoise at 23° C.

2. The composition of claim 1 wherein the hydrophobic group of each emulsifier comprises an alkyl group of at least 12 carbon atoms; an alkenyl group of at least 12 carbon atoms; or an aralkyl or an aralkenyl group of at least 14 carbon atoms.

3. The composition of claim 2 wherein at least one of the emulsifiers has at least one alkyl group of at least 18 carbon atoms.

4. The composition of claim 1 wherein at least one of the emulsifiers has an average alkyl chain length of at least 18 carbon atoms when the weight ratio of lower alcohol to water is greater than about 50:50.

5. The composition of claim 1 wherein at least one of the emulsifiers is solid at ambient temperature.

6. The composition of claim 5 wherein the hydrophobic group of the solid emulsifier comprises a saturated straight chain hydrocarbon group of at least 14 carbon atoms.

7. The composition of claim 6 wherein the emulsifier that comprises a saturated straight chain hydrocarbon group of at least 14 carbon atoms is selected from the group consisting of an alkyl alcohol, an alkyl polyglucoside, a polyglycerol alkyl ester, a C1–C4 ester of an alkyl alcohol, a C1–C4 ester of an alkyl carboxylate, an alkyl amide, an alkyl betaine, an alkyl phosphate or phospholipid, an alkyl quaternary amine, an alkyl amine oxide, a polyethoxylated alkyl alcohol, an alkyl ester of polyethylene glycol, and mixtures thereof.

8. The composition of claim 1 wherein the hydrophilic group comprises:

(a) an amide group having the structure —NHC(O)R''' or —C(O)NHR''' where R''' is hydrogen or an alkyl group of 1–10 carbon atoms optionally substituted in available positions by N, O and S atoms;
   (b) an ester group of C1–C4 alcohols or acids;
   (c) a polyglucoside group having 1–10 glucose units;
   (d) a polyglycerol ester group having 1–15 glycerol units;
   (e) a secondary amine group, tertiary amine group, or quaternary amine group;
   (f) an anionic group;
   (g) a zwitterionic group having the formula

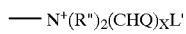

or

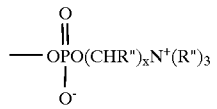

wherein each R'' is independently hydrogen or an alkyl group having 1–4 carbon atoms or alkenyl group having 2–4 carbon atoms, which alkyl or alkenyl groups are optionally substituted with nitrogen, oxygen, or sulfur atoms, including alkyl or alkenyl carboxyl groups; Q is hydrogen or hydroxyl; x is 1 to 4; and L' is —CO$_2^-$, —OP(O)(O$^-$)(O$^-$M$^+$), —(O)P(OR''')(O)(O$^-$M$^+$) where R''' is hydrogen or an alkyl group of 1–10 carbon atoms optionally substituted in available positions by N, O, or S atoms, —SO$_2$O$^-$, or —OSO$_2$O$^-$, where M$^+$ is a positively charged counterion present in a molar ratio necessary to achieve a net neutral charge on the emulsifier and is selected from the group of hydrogen, sodium, potassium, lithium, ammonium, calcium, magnesium, or N$^+$R'$_4$ where each R' is independently an alkyl group of 1 to 4 carbon atoms optionally substituted with N, O, or S atoms;

(h) an alcohol group;

(i) an ethylene oxide- and/or propylene oxide-containing group having 2–150 moles of ethylene oxide plus propylene oxide per mole of hydrophobe ("R") and bonded to the hydrophobe through an ether of ester linkage, and optionally terminated by C1–C36 alkyl or C6 to C36 alkaryl ester;

(j) an ester or ether group of polyhydric alcohol and their polyethoxylated derivatives;

(k) an ester or ether of sorbitan or polyethoxylated sorbitan group; and (l) combinations of these groups.

9. The composition of claim 1 wherein the emulsifier system is present in an amount of about 0.5% to about 30% by weight, based on the total weight of the composition.

10. The composition of claim 1 wherein the emulsifier system comprises at least one nonionic emulsifier and has a weight average hydrophile/lipophile balance of about 2 to about 20.

11. The composition of claim 1 wherein the emulsifier system comprises an alkyl alcohol and an alkyl polyethoxylate.

12. The composition of claim 1 wherein the emulsifier system comprises an alkyl polyglucoside and an alkyl polyethoxylate.

13. The composition of claim 1 further comprising at least one emollient.

14. The composition of claim 13 wherein the emollient is selected from the group consisting of a wax, an oil, a humectant, and mixtures thereof.

15. The composition of claim 1 wherein the weight ratio of lower alcohol to water is at least about 50:50.

16. The composition of claim 1 further comprising a penetration enhancer.

17. The composition of claim 16 wherein the secondary penetration enhancer is selected from the group consisting of C$_8$–C$_{22}$ fatty acids, C$_8$–C$_{22}$ fatty alcohols, lower alkyl esters of C$_8$–C$_{22}$ fatty acids, di(lower)alkyl esters of C$_6$–C$_8$ diacids, monoglycerides of C$_8$–C$_{22}$ fatty acids, tetrahydrofurfuryl alcohol polyethylene glycol ether, polyethylene glycol, propylene glycol, 2-(2-ethoxyethoxy)ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethyl acetate, acetoacetic ester, N-alkylpyrrolidone, and terpenes.

18. The composition of claim 1 wherein the lower alcohol is selected from the group consisting of ethanol, 2-propanol, n-propanol, and mixtures thereof.

19. The composition of claim 1 wherein the viscosity is at least about 10,000 centipoise.

20. The composition of claim 19 wherein the viscosity is at least about 50,000 centipoise.

21. The composition of claim 1 further comprising an additive selected from the group consisting of a stabilizer, a salt, an antimicrobial agent, a fragrance, and mixtures thereof.

22. The composition of claim 1 further comprising a polymeric thickening agent.

23. The composition of claim 1 wherein the pharmaceutical agent is selected from the group consisting of antiinflammatory drugs, antibacterials, antiprotazoals, vasodialtors, calcium channel blockers, bronchodilators, enzyme inhibitors, antihypertensives, leukotriene antagonists, antiulceratives, steroidal hormones, antivirals, immunomodulators, local anesthetics, antitussives, antihistamines, narcotic analgesics, peptide hormones, cardioactive products, proteinaceous products, enzymes, antinauseants, anticonvulsants, immunosuppressives, psychotherapeutics, sedatives, anticoagulants, analgesics, antimigraine agents, antiarrhythmic agents, antiemetics, anticancer agents, neurologic agents, hemostatics, antiobesity agents, nicotine, as well as pharmaceutically acceptable salts and esters thereof.

24. The composition of claim 1 which has a cumulative flux of at least three times that of the same pharmaceutical agent in water.

25. The composition of claim 1 which does not separate more than about 10% by volume when centrifuged for 30 minutes at 1545×g.

26. A hydroalcoholic composition useful for the enhancement of the transdermal delivery of a pharmaceutical agent through the skin and into the circulatory system of a patient, the composition comprising:

(a) a lower alcohol, which is a C1–C4 alcohol, and water in a weight ratio of at least about 20:80;

(b) a pharmaceutical agent; and (c) an emulsifier system comprising at least two emulsifiers present in an amount of at least about 0.05% by weight, based on the total weight of the composition; wherein each emulsifier is a compound of the formula (R)$_a$(L)$_b$ wherein "R" represents a hydrophobic group, "L" represents a hydrophilic group, and "a" and "b" are independently 1–4, and at least one emulsifier is further of the formula:

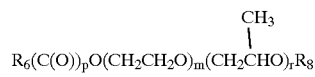

wherein R$_6$ is a straight or branched alkyl or alkenyl hydrocarbon chain of at least 12 carbon atoms, m=0–200, p=0 or 1, and r=0–50, and R$_8$=H or —C(O)—R$_{12}$, wherein R$_{12}$ is an alkyl group of 1–36 carbon atoms optionally substituted by N, O or S, or an aralkyl group of 6 to 36 carbon atoms; and further wherein the emulsifier system is selected such that the composition, when free of auxiliary thickeners, has a viscosity of at least about 4,000 centipoise at 23° C.

27. The composition of claim 26 which does not separate more than about 10% by volume when centrifuged for 30 minutes at 1545×g.

28. A transdermal delivery system comprising:

(a) a hydroalcoholic composition useful for the enhancement of the transdermal delivery of a pharmaceutical agent through the skin and into the circulatory system of a patient, the composition comprising:

(i) a lower alcohol, which is a C1–C4 alcohol, and water in a weight ratio of at least about 20:80;

(ii) a pharmaceutical agent; and (iii) an emulsifier system comprising at least two emulsifiers, each emulsifier being present in an amount of at least about 0.05% by weight, based on the total weight of the composition; wherein each emulsifier:

(A) is of the formula $(R)_a(L)_b$ wherein "R" represents a hydrophobic group, "L" represents a hydrophilic group, and "a" and "b" are independently 1–4; and (B) is selected such that the composition, when free of auxiliary thickeners, has a viscosity of at least about 4,000 centipoise at 23° C.; and (b) means for delivery of the composition to the skin of a patient.

29. The transdermal delivery system of claim 28 wherein the means for delivery is the composition itself in the form of a lotion.

30. The transdermal delivery system of claim 29 wherein the means for delivery of the composition comprises a reservoir device.

31. The transdermal delivery system of claim 28 wherein the composition does not separate more than about 10% by volume when centrifuged for 30 minutes at 1545×g.

32. The transdermal delivery system of claim 28 wherein the emulsifier system comprises an emulsifier having at least one hydrophobic group comprising an alkyl group of at least 12 carbon atoms; an alkenyl group of at least 12 carbon atoms; or an aralkyl or an aralkenyl group of at least 14 carbon atoms.

33. The transdermal delivery system of claim 28 wherein the emulsifier system comprises an emulsifier selected from the group of an alkyl alcohol, an alkyl polyglucoside, a polyglycerol alkyl ester, a C1–C4 ester of an alkyl alcohol, a C1–C4 ester of an alkyl carboxylate, an alkyl amide, an alkyl betaine, an alkyl phosphate or phospholipid, an alkyl quaternary amine, an alkyl amine oxide, a polyethoxylated alkyl alcohol, an alkyl ester of polyethylene glycol, and mixtures thereof.

34. The transdermal delivery system of claim 28 wherein the emulsifier system comprises an emulsifier having at least one hydrophilic group comprising:

(a) an amide group having the structure —NHC(O)R''' or —C(O)NHR''' where R''' is hydrogen or an alkyl group of 1–10 carbon atoms optionally substituted in available positions by N, O and S;

(b) an ester group of C1–C4 alcohols or acids;

(c) a polyglucoside group having 1–10 glucose units;

(d) a polyglycerol ester group having 1–15 glycerol units;

(e) a secondary amine group, tertiary amine group, or quaternary amine group;

(f) an anionic group;

(g) a zwitterionic group having the formula

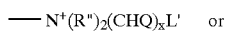

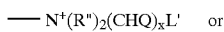

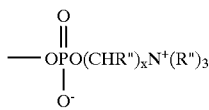

wherein each R" is independently hydrogen or an alkyl group having 1–4 carbon atoms or alkenyl group having 2–4 carbon atoms, which alkyl or alkenyl groups are optionally substituted with nitrogen, oxygen, or sulfur atoms, including alkyl or alkenyl carboxyl groups; Q is hydrogen or hydroxyl; x is 1 to 4; and L' is —$CO_2^-$, —OP(O)($O^-$)($O^-M^+$), —(O)P(OR''')(O)($O^-M^+$) where R''' is hydrogen or an alkyl group of 1–10 carbon atoms optionally substituted in available positions by N, O, or S atoms, —$SO_2O^-$, or —$OSO_2O^-$, where $M^+$ is a positively charged counterion present in a molar ratio necessary to achieve a net neutral charge on the emulsifier and is selected from the group of hydrogen, sodium, potassium, lithium, ammonium, calcium, magnesium, or $N^+R'_4$ where each R' is independently an alkyl group of 1 to 4 carbon atoms optionally substituted with N, O, or S atoms;

(h) an alcohol group;

(i) an ethylene oxide- and/or propylene oxide-containing group having 2–150 moles of ethylene oxide plus propylene oxide per mole of hydrophobe ("R") and bonded to the hydrophobe through an ether of ester linkage, and optionally terminated by C1–C36 alkyl or C6 to C36 alkaryl ester;

(j) an ester or ether group of polyhydric alcohol and their polyethoxylated derivatives;

(k) an ester or ether of sorbitan or polyethoxylated sorbitan group; and (l) combinations of these groups.

35. The transdermal delivery system of claim 28 wherein the emulsifier system comprises an alkyl alcohol and an alkyl polyethoxylate.

36. The transdermal delivery system of claim 28 wherein the emulsifier system comprises an alkyl polyglucoside and an alkyl polyethoxylate.

37. A transdermal delivery system comprising:

(a) a hydroalcoholic composition useful for the enhancement of the transdermal delivery of a pharmaceutical agent through the skin and into the circulatory system of a patient, the composition comprising:

(i) a lower alcohol, which is a C1–C4 alcohol, and water in a weight ratio of at least about 20:80;

(ii) a pharmaceutical agent; and (iii) an emulsifier system comprising at least two emulsifiers present in an amount of at least about 0.05% by weight, based on the total weight of the composition; wherein each emulsifier is a compound of the formula $(R)_a(L)_b$ wherein "R" represents a hydrophobic group, "L" represents a hydrophilic group, and "a" and "b" are independently 1–4, and at least one emulsifier is further of the formula:

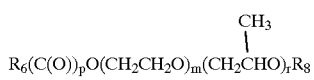

wherein $R_6$ is a straight or branched alkyl or alkenyl hydrocarbon chain of at least 12 carbon atoms, m=0–200, p=0 or 1, and r=0–50, and $R_8$=H or —C(O)—$R_{12}$, wherein $R_{12}$ is an alkyl group of 1–36 carbon atoms optionally substituted by N, O or S, or an aralkyl group of 6 to 36 carbon atoms; and further wherein the emulsifier system is selected such that the composition, when free of auxiliary thickeners, has a viscosity of at least about 4,000 centipoise at 23° C.; and (b) means for delivery of the composition to the skin of a patient.

38. The transdermal delivery system of claim 37 wherein the means for delivery is the composition itself in the form of a lotion.

39. A method of preparing a hydroalcoholic composition, the method comprising:

preparing an emulsifier system comprising at least two emulsifiers, each emulsifier being present in an amount of at least about 0.05% by weight, based on the total weight of the composition; wherein each emulsifier is of the formula $(R)_a(L)_b$ wherein "R" represents a hydrophobic group, "L" represents a hydrophilic group, and "a" and "b" are independently 1–4 and is selected such that the resultant hydroalcoholic composition, when free of auxiliary thickeners, has a viscosity of at least about 4,000 centipoise at 23° C.; and combining a hydroalcoholic solvent system with the emulsifier system and a pharmaceutical agent for form a hydroalcoholic composition useful for the enhancement of the transdermal delivery of a pharmaceutical agent through the skin and into the circulatory system of a patient.

40. The method of claim 39 wherein the step of combining comprises:
    combining the hydroalcoholic solvent system with the emulsifier system at a temperature sufficient to melt the emulsifier system;
    cooling and emulsifier system/hydroalcoholic solvent combination to less than about 30° C.; and
    adding the pharmaceutical agent.

41. The method of claim 40 wherein the step of adding the pharmaceutical agent occurs prior to the step of cooling the emulsifier/hydroalcoholic solvent combination.

42. A method of preparing a hydroalcoholic composition, the method comprising:
    preparing an emulsifier system to a temperature sufficient to melt the emulsifier system, wherein the emulsifier comprises at least two emulsifiers, each emulsifier being present in an amount of at least about 0.05% by weight, based on the total weight of the composition; wherein each emulsifier is of the formula $(R)_a(L)_b$ wherein "R" represents a hydrophobic group, "L" represents a hydrophilic group, and "a" and "b" are independently 1–4 and is selected such that the resultant hydroalcoholic composition, when free of auxiliary thickeners, has a viscosity of at least about 4,000 centipoise at 23° C.;
    combining the heated emulsifier system with water;
    adding a lower chain alcohol, which is a C1–C4 alcohol, to the water/emulsifier system; and
    adding a pharmaceutical agent to form a hydroalcoholic composition useful for the enhancement of the transdermal delivery of a pharmaceutical agent through the skin and into the circulatory system of a patient.

43. The method of claim 42 wherein the step of adding the pharmaceutical agent occurs prior to the step of combining the heated emulsifier system with water.

44. A method of preparing a hydroalcoholic composition, the method comprising:
    preparing an emulsifier system comprising at least two emulsifiers present in an amount of at least about 0.05% by weight, based on the total weight of the composition; wherein each emulsifier is a compound of the formula $(R)_a(L)_b$ wherein "R" represents a hydrophobic group, "L" represents a hydrophilic group, and "a" and "b" are independently 1–4, and at least one emulsifier is further of the formula:

wherein $R_6$ is a straight or branched alkyl or alkenyl hydrocarbon chain of at least 12 carbon atoms, m=0–200, p=0 or 1, and r=0–50, and $R_8$=H or —C(O)—$R_{12}$, wherein $R_{12}$ is an alkyl group of 1–36 carbon atoms optionally substituted by N, O or S, or an aralkyl group of 6 to 36 carbon atoms; and the emulsifier system is selected such that the resultant hydroalcoholic composition, when free of auxiliary thickeners, has a viscosity of at least about 4,000 centipoise at 23° C.; and combining a hydroalcoholic solvent system with the emulsifier system and a pharmaceutical agent to form a hydroalcoholic composition useful for the enhancement of the transdermal delivery of a pharmaceutical agent through the skin and into the circulatory system of a patient.

45. The method of claim 44 wherein the step of combining comprises:
    combining the hydroalcoholic solvent system with the emulsifier system at a temperature sufficient to melt the emulsifier system;
    cooling the emulsifier system/hydroalcoholic solvent combination to less than about 30° C.; and
    adding the pharmaceutical agent.

46. The method of claim 45 wherein the step of adding the pharmaceutical agent occurs prior to the step of cooling the emulsifier/hydroalcoholic solvent combination.

47. A method of preparing a hydroalcoholic composition, the method comprising:
    heating an emulsifier system to a temperature sufficient to melt the emulsifier system, wherein the emulsifier system comprises at least two emulsifiers present in an amount of at least about 0.05% by weight, based on the total weight of the composition; wherein each emulsifier is a compound of the formula $(R)_a(L)_b$ wherein "R" represents a hydrophobic group, "L" represents a hydrophilic group, and "a" and "b" are independently 1–4, and at least one emulsifier is further of the formula:

wherein $R_6$ is a straight or branched alkyl or alkenyl hydrocarbon chain of at least 12 carbon atoms, m=0–200, p=0 or 1, and r=0–50, and $R_8$=H or —C(O)—$R_{12}$, wherein $R_{12}$ is an alkyl group of 1–36 carbon atoms optionally substituted by N, O or S, or an aralkyl group of 6 to 36 carbon atoms; and the emulsifier system is selected such that the resultant hydroalcoholic composition, when free of auxiliary thickeners, has a viscosity of at least about 4,000 centipoise at 23° C.;
    combining the heated emulsifier system with water;
    adding a lower chain alcohol, which is a C1–C4 alcohol, to the water/emulsifier system; and
    adding a pharmaceutical agent to form a hydroalcoholic composition useful for the enhancement of the transdermal delivery of a pharmaceutical agent through the skin and into the circulatory system of a patient.

48. A method of delivering a pharmaceutical agent transdermally to a patient, the method comprising:
    preparing a hydroalcoholic composition comprising: a lower alcohol, which is a C1–C4 alcohol, and water in a weight ratio of at least about 20:80; a pharmaceutical agent; and an emulsifier system comprising at least two emulsifiers, each emulsifier being present in an amount of at least about 0.05% by weight, based on the total weight of the composition; wherein each emulsifier: is of the formula $(R)_a(L)_b$ wherein "R" represents a hydrophobic group, "L" represents a hydrophilic group, and "a" and "b" are independently 1–4; and is selected such that the composition, when free of auxiliary thickeners, has a viscosity of at least about 4,000 centipoise at 23° C.; and applying the hydroalcoholic composition to the skin of a patient for delivery for the pharmaceutical agent through the patient's skin and into the patient's circulatory system.

49. The method of claim 48 wherein the hydroalcoholic composition does not separate more than about 10% by volume when centrifuged for 30 minutes at 1545×g.

50. The method of claim 48 further including incorporating the hydroalcoholic composition into a reservoir device prior to the step of applying the composition to the skin of a patient.

51. A method of delivering a pharmaceutical agent transdermally to a patient, the method comprising:

preparing a hydroalcoholic composition comprising; a lower alcohol, which is a C1–C4 alcohol, and water in a weight ratio of at least about 20:80; a pharmaceutical agent; and an emulsifier system comprising at least two emulsifiers present in an amount of at least about 0.05% by weight, based on the total weight of the composition; wherein each emulsifier is a compound of the formula $(R)_a(L)_b$ wherein "R" represents a hydrophobic group, "L" represents a hydrophilic group, and "a" and "b" are independently, 1–4 and at least one emulsifier is further of the formula:

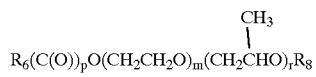

wherein $R_6$ is a straight or branched alkyl or alkenyl hydrocarbon chain of at least 12 carbon atoms, m=0–200, p=0 or 1, and r=0–50, and $R_8$=H or —C(O)—$R_{12}$, wherein $R_{12}$ is an alkyl group of 1–36 carbon atoms optionally substituted by N, O or S, or an aralkyl group of 6 to 36 carbon atoms; wherein the hydroalcoholic composition does not separate more than about 10% by volume when centrifuged for 30 minutes at 1545×g; and further wherein the emulsifier system is selected such that the composition, when free of auxiliary thickeners, has a viscosity of at least about 4,000 centipoise at 23° C.; and applying the hydroalcoholic composition to the skin of a patient for delivery of the pharmaceutical agent through the patient's skin and into the patient's circulatory system.

52. A hydroalcoholic composition useful for the enhancement of the transdermal delivery of a pharmaceutical agent through the skin and into the circulatory system of a patient, the composition is prepared by combining components comprising:

(a) a lower alcohol, which is a C1–C4 alcohol, and water in a weight ratio of at least about 20:80;

(b) a pharmaceutical agent; and (c) an emulsifier system comprising at least two emulsifiers, each emulsifier being present in an amount of at least about 0.05% by weight, based on the total weight of the composition; wherein each emulsifier:

(i) is of the formula $(R)_a(L)_b$ wherein "R" represents a hydrophobic group, "L" represents a hydrophilic group, and "a" and "b" are independently 1–4; and (ii) is selected such that the composition, when free of auxiliary thickeners, has a viscosity of at least about 4,000 centipoise at 23° C.

53. A hydroalcoholic composition useful for the enhancement of the transdermal delivery of a pharmaceutical agent through the skin and into the circulatory system of a patient, the composition prepared by combining components comprising:

(a) a lower alcohol, which is a C1–C4 alcohol, and water in a weight ratio of at least about 20:80;

(b) a pharmaceutical agent; and (c) an emulsifier system comprising at least two emulsifiers present in an amount of at least about 0.05% by weight, based on the total weight of the composition; wherein each emulsifier is a compound of the formula $(R)_a(L)_b$ wherein "R" represents a hydrophobic group, "L" represents a hydrophilic group, and "a" and "b" are independently 1–4, and at least one emulsifier is further of the formula:

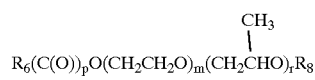

wherein $R_6$ is a straight or branched alkyl or alkenyl hydrocarbon chain of at least 12 carbon atoms, m=0–200, p=0 or 1, and r=0–50, and $R_8$=H or —C(O)—$R_{12}$, wherein $R_{12}$ is an alkyl group of 1–36 carbon atoms optionally substituted by N, O or S, or an aralkyl group of 6 to 36 carbon atoms; and further wherein the emulsifier system is selected such that the composition, when free of auxiliary thickeners, has a viscosity of at least about 4,000 centipoise at 23° C.

54. A transdermal delivery system comprising:

(a) a hydroalcoholic composition useful for the enhancement of the transdermal delivery of a pharmaceutical agent, the composition prepared by combining components comprising:

(i) a lower alcohol, which is a C1–C4 alcohol, and water in a weight ratio of at least about 20:80;

(ii) a pharmaceutical agent; and (iii) an emulsifier system comprising at least two emulsifiers, each emulsifier being present in an amount of at least about 0.05% by weight, based on the total weight of the composition; wherein each emulsifier:

(A) is of the formula $(R)_a(L)_b$ wherein "R" represents a hydrophobic group, "L" represents a hydrophilic group, and "a" and "b" are independently 1–4; and (B) is selected such that the composition, when free of auxiliary thickeners, has a viscosity of at least about 4,000 centipoise at 23° C.; and (b) means for delivery of the composition to the skin of a patient for delivery of the pharmaceutical agent through the patient's skin and into the patient' circulatory system.

55. A transdermal delivery system comprising:

(a) a hydroalcoholic composition useful for the enhancement of the transdermal delivery of a pharmaceutical agent, the composition preparable by combining components comprising:

(i) a lower alcohol, which is a C1–C4 alcohol, and water in a weight ratio of at least about 20:80;

(ii) a pharmaceutical agent; and (iii) an emulsifier system comprising at least two emulsifiers present in an amount of at least about 0.05% by weight, based on the total weight of the composition; wherein each emulsifier is a compound of the formula $(R)_a(L)_b$ wherein "R" represents a hydrophobic group, "L" represents a hydrophilic group, and "a" and "b" are independently 1–4, and at least one emulsifier is further of the formula:

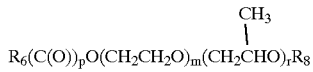

wherein $R_6$ is a straight or branched alkyl or alkenyl hydrocarbon chain of at least 12 carbon atoms, m=0–200, p=0 or 1, and r=0–50, and $R_8$=H or —C(O)—$R_{12}$, wherein $R_{12}$ is an alkyl group of 1–36 carbon atoms optionally substituted by N, O or S, or an aralkyl group of 6 to 36 carbon atoms; and further wherein the emulsifier system is selected such that the composition, when free of auxiliary thickeners, has a viscosity of at least about 4,000 centipoise at 23° C.; and (b) means for delivery of the composition to the skin of a patient for delivery of the pharmaceutical agent through the patient's skin and into the patient's circulatory system.

56. A method of dispensing the composition of claim 1 comprising dispensing the composition as a lotion in precise amounts to the skin of a patient using a dispenser.

* * * * *